(12) United States Patent
Ebersole et al.

(10) Patent No.: US 6,797,817 B1
(45) Date of Patent: Sep. 28, 2004

(54) NUCLEIC ACID FRAGMENTS FOR THE IDENTIFICATION OF DECHLORINATING BACTERIA

(75) Inventors: Richard C. Ebersole, Wilmington, DE (US); Edwin R. Hendrickson, Hockessin, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 09/548,998

(22) Filed: Apr. 14, 2000

Related U.S. Application Data

(60) Provisional application No. 60/129,511, filed on Apr. 15, 1999.

(51) Int. Cl.[7] ............................................. C07H 21/04
(52) U.S. Cl. .................... 536/24.3; 435/243; 435/262.5
(58) Field of Search ........................ 536/24.3; 435/243, 435/262.5

(56) References Cited

U.S. PATENT DOCUMENTS

| | | |
|---|---|---|
| 4,851,330 A | 7/1989 | Kohne |
| 5,540,838 A | 7/1996 | Smullen et al. |
| 5,574,145 A | 11/1996 | Barry et al. |

FOREIGN PATENT DOCUMENTS

| | | |
|---|---|---|
| EP | 0 864 542 A2 | 9/1998 |
| FR | 2 733 754 A | 11/1996 |
| WO | WO 89/06704 | 7/1989 |
| WO | WO 98 49106 A1 | 11/1998 |
| WO | WO 0063443 A2 | 10/2000 |

OTHER PUBLICATIONS

Maymó–Gatell et al (1997) Science 276:1568–1571.*
Holoman Tracey R. Pulliam et al., "Characterization of a defined 1,3,5,6–tettrachlorobiphenyl–ortho–dechlorinating microbial community by comparative sequence analysis of genes coding for 16S rRNA." Applied and Environmental Microbiology, vol. 64, No. 9, 1988, pp. 3359–3367, XP002179677.
Von Wintzingerode Friedrich et al., "Phylogenetic analysis of an anaerobic, trichlorobenzene–transforming microbial consortium." Applied and Environmental Microbiology, vol., 65, No. 1, Jan. 1999, pp. 283–286, XP002179579.
Lamontagne M. G. et al., "Identification and analysis of PCB dechlorinating anaerobic enrichments by amplification: Accuracy of community structure based on restriction analysis and partial sequencing of 16S rRNA genes." Journal of Applied Microbiology, vol. 84, No. 8, Jun. 1998, pp. 1156–1162, XP001024984.
Löffler et al., 16S rRNA gene–based detection of tetrachloroethene–dechlorinating Desulfuromonas and Dehalococcoides species, Applied and Environmental Microbiology, vol. 66, No. 4, Apr. 2000, pp. 1369–1374, XP002215287.
Eberson et al., Detection of dechlorinating bacteria in groundwater and soils from waste sites contaminated with PCE and TCE, Abstracts in Environmental and General Applied Microbiology, vol. 99, May 30, 1999, pp. 539, XP008008413.
Carrol et al., The molecular detection of Dehalococcoides ethenogenes in PCR and TCE–contaminated sites by PCR, Abstracts in Environmental and General Applied Microbiology, vol. 90, May 30, 1999, Jun. 3, 1999, XP008008415.
Ritalahti et al., Dehalococcoides–like population detected in 1,2–dichloropropane dechlorinating enrichment cultures, Abstracts of the American Society for Microbiology, vol. 101, pp. 20, May 24, 2001, XP002216099.
Biswas, N. et al.,Water Environ. Res. 64: 170–178 (1992).
Hutter, G. M. et al., Water Environ. Res. 64:69–77 (1992).
Vogel, T. M., Environ. Sci. Technol., 21:722–736 (1987).
Kochian., Plant Mol. Biol., 46:237–245 (1995).
Delhaize et al., Plant Physiol. 107:315–321 (1995).
Freedman et al., Appl. Environ. Microbiol. 55:2144–2151 (1989).
Maymó–Gatell et al., Science, 176:1568–1571 (1997).
Woese, Scientific American 244 (6):98–122 1981.

\* cited by examiner

Primary Examiner—James Ketter
Assistant Examiner—David A. Lambertson

(57) ABSTRACT

A 16S rRNA profile derived from *Dehalococcoides ethenogenes* has been identified and isolated. The profile contains several nucleic acid fragments that are linked to dechlorinating activity. These sequences are set forth in SEQ ID NO:1, SEQ ID NO:8, SEQ ID NO:30 and SEQ ID NO:34.

1 Claim, 20 Drawing Sheets

The *Dehalococcoides sp.* alignment

```
DHE seq alignments1.msf   MSF: 1223

Name: DHE.(cornell)
Name: DHE.(stf).seq
Name: DHE.(pl ).seq
Name: DHE.(dll).seq
Name: DHE.(dab).seq
Name: DHE.(pin).seq
//
//

1                                                            60
DHE.(cornell)    GATGAACGCTAGCGGCGCGTGCCTTATGCATGCAAGTCGAACGGTCTTAAGCAATTAAGATA
DHE.(stf).seq    GATGAACGCTAGCGGCGCGTGCCTTATGCATGCAAGTCGAACGGTCTTAAGCAATTAAGATA
DHE.(pl ).seq    GATGAACGCTAGCGGCGCGTGCCTTATGCATGCAAGTCGAACGGTCTTAAGCAATTAAGATA
DHE.(dll).seq    GATGAACGCTAGCGGCGCGTGCCTTATGCATGCAAGTCGAACGGTCTTAAGCAATTAAGATA
DHE.(dab).seq    GATGAACGCTAGCGGCGCGTGCCTTATGCATGCAAGTCGAACGGTCTTAAGCAATTAAGATA
DHE.(pin).seq    GATGAACGCTAGCGGCGCGTGCCTTATGCATGCAAGTCGAACGGTCTTAAGCAATTAAGATA 61                                                           120
DHE.(cornell)    GTGGCAAACGGGTGAGTAACGCGTAAGTAACCTACCTCTAAGTGGGGATAGCTTCGGGA
DHE.(stf).seq    GTGGCAAACGGGTGAGTAACGCGTAAGTAACCTACCTCTAAGTGGGGATAGCTTCGGGA
DHE.(pl ).seq    GTGGCAAACGGGTGAGTAACGCGTAAGTAACCTACCTCTAAGTGGGGATAGCTTCGGGA
DHE.(dll).seq    GTGGCAAACGGGTGAGTAACGCGTAAGTAACCTACCTCTAAGTGGGGATAGCTTCGGGA
DHE.(dab).seq    GTGGCGAACGGGTGAGTAACGCGTAAGTAACCTACCTCTAAGTGGGGATAGCTTCGGGA
DHE.(pin).seq    GTGGCGAACGGGTGAGTAACGCGTAAGTAACCTACCTCTAAGTGGGGATAGCTTCGGGA
```

FIG. 1A

```
                      121                                                    180
DHE.(cornell)         AACTGAAGGTAATACCCGCATGTGATGGGCTGACACATAAGTCGGTTCATTAAAGCCGCAAGG
DHE.(stf).seq         AACTGAAGGTAATACCCGCATGTGATGGGCTGACACATAAGTCGGTTCATTAAAGCCGTAAGG
DHE.(pl ).seq         AACTGAAGGTAATACCCGCATGTGATGGGCCGACACATAAGTTGGTTCACTAAAGCCGTAAGG
DHE.(dll).seq         AACTGAAGGTAATACCCGCATGTGATGGGCCGACACATAAGTCGGTTCACTAAAGCCGTAAGG
DHE.(dab).seq         AACTGAAGGTAATACCCGCATGTGATGGGCCGACACATGTTGGTTCACTAAAGCCGTAAGG
DHE.(pin).seq         AACTGAAGGTAATACCCGCATGTGGTGGGCCGACACATGTTGGTTCACTAAAGCCGTAAGG 181                                                    240
DHE.(cornell)         TGCTTGGTGAGGGGCTTGCGTCCGATTAGCTAGTTGGTGGGGTAATGGTCTACCAAGGCT
DHE.(stf).seq         TGCTTGGTGAGGGGCTTGCGTCCGATTAGCTAGTTGGTGGGGTAATGGTCTACCAAGGCT
DHE.(pl ).seq         TGCTTGGTGAGGGGCTTGCGTCCGATTAGCTAGTTGGTGGGGTAACGGCCTACCAAGGCT
DHE.(dll).seq         TGCTTGGTGAGGGGCTTGCGTCCGATTAGCTAGTAGTTGGTGGGGTAATGGCCTACCAAGGCT
DHE.(dab).seq         TGCTTGGTGAGGGGCTTGCGTCCGATTAGCTAGTAGTTGGTGGGGTAACGGCCTACCAAGGCT
DHE.(pin).seq         CGCTTGGTGAGGGGCTTGCGTCCGATTAGCTAGTAGTTGGTGGGGTAATGGCCTACCAAGGCT 241                                                    300
DHE.(cornell)         TCGATCGGTAGCT.GGTCTGAGAGGATGATCAGCCACACTGGGACTGAGACACGGGCCAG
DHE.(stf).seq         TCGATCGGTAGCT.GGTCTGAGAGGATGATCAGCCACACTGGGACTGAGACACGGGCCCAG
DHE.(pl ).seq         TCGATCGGTAGCT.GGTCTGAGAGAGGATGATCAGCCACACTGGGACTGAGACACGGCCCAG
DHE.(dll).seq         TCGATCGGTAGCT.GGTCTGAGAGAGGATGATCAGCCACACTGGGACTGAGACACGGCCCAG
DHE.(dab).seq         TCGATCGGTAGCT.GGTCTGAGAGAGGATGATCAGCCACACTGGGACTGAGACACGGCCCAG
DHE.(pin).seq         TCGATCGGTAGCT.GGTCTGAGAGAGGATGATCAGCCACACTGGGACTGAGACACGGCCCAG
```

FIG. 1B

```
              301                                                        360
DHE.(cornell) ACTCCTACGGAGGCAGCAGCAAGCAGCAAGGAATCTTGGGCAATGGGCGAAAGCCTGACCCAGCAA
DHE.(stf).seq ACTCCTACGGAGGCAGCAGCAGCAGCAAGGAATCTTGGGCAATGGGCGAAAGCCTGACCCAGCAA
DHE.(pl ).seq ACTCCTACGGAGGCAGCAGCAGCAGCAAGGAATCTTGGGCAATGGGCGAAAGCCTGACCCAGCAA
DHE.(dll).seq ACTCCTACGGAGGCAGCAGCAGCAGCAAGGAATCTTGGGCAATGGGCGAAAGCCTGACCCAGCAA
DHE.(dab).seq ACTCCTACGGAGGCAGCAGCAGCAGCAAGGAATCTTGGGCAATGGGCGAAAGCCTGACCCAGCAA
DHE.(pin).seq ACTCCTACGGAGGCAGCAGCAGCAGCAAGGAATCTTGGGCAATGGGCGAAAGCCTGACCCAGCAA 361                                                        420
DHE.(cornell) CGCCGCGTGAGGGATGAAGGCTTTCGGGTTGTAAACCTCTTTTCACAGGGAAGAATAATG
DHE.(stf).seq CGCCGCGTGAGGGATGAAGGCTCTCGGGTTGTAAACCTCTTTTCACAGGGAAGAATAATG
DHE.(pl ).seq CGCCGCGTGAGGGATGAAGGCTTTCGGGTTGTAAACCTCTTTTCACAGGGAAGAATAATG
DHE.(dll).seq CGCCGCGTGAGGGATGAAGGCTTTCGGGTTGTAAACCTCTCTTTCACAGGGAAGAATAATG
DHE.(dab).seq CGCCGCGTGAGGGATGAAGGCTTTCGGGTTGTAAACCTCTTTTCATAGGGAAGAATAATG
DHE.(pin).seq CGCCGCGTGAGGGATGAAGGCTTTCGGGTTGTAAACCTCTTTTCATAGGGAAGAATAATG 421                                                        480
DHE.(cornell) ACGGTACCTGTGGAATAAGCTTCGGCTAACTACGTGCCAGCAGCCGCGGTAATACGTAGG
DHE.(stf).seq ACGGTACCTGTGGAATAAGCTTCGGCTAACTACGTGCCAGCAGCCGCGGTAATACGTAGG
DHE.(pl ).seq ACGGTACCTGTGGAATAAGCTTCGGCTAACTACGTGCCAGCAGCCGCGGTAATACGTAGG
DHE.(dll).seq ACGGTACCTGTGGAATAAGCTTCGGCTAACTACGTGCCAGCAGCCGCGGTAATACGTAGG
DHE.(dab).seq ACGGTACCTGTGGAATAAGCTTCGGCTAACTACGTGCCAGCAGCCGCGGTAATACGTAGG
DHE.(pin).seq ACGGTACCTGTGGAATAAGCTTCGGCTAACTACGTGCCAGCAGCCGCGGTAATACGTAGG
```

FIG. 1C

```
              481
DHE.(cornell)    GAAGCAAGCGTTATCCGGATTTATTGGGCGTAAAGTGAGCGTAGGTGGTCTTTCAAGTTG   540
DHE.(stf).seq    .AAGCAAGCGTTATCCGGATTTATTGGGCGTAAAGTGAGCGTAGGTGGTCTTTCAAGTTG
DHE.(pl ).seq    .AAGCAAGCGTTATCCGGATTTATTGGGCGTAAAGTGAGCGTAGGTGGTCTTTCAAGTTG
DHE.(dll).seq    .AAGCAAGCGTTATCCGGATTTATTGGGCGTAAAGTGAGCGTAGGTGGTCTTTCAAGTTG
DHE.(dab).seq    .AAGCAAGCGTTATCCGGATTTATTGGGCGTAAAGTGAGCGTAGGTGGTCTTTCAAGTTG
DHE.(pin).seq    .AAGCAAGCGTTATCCGGATTTATTGGGCGTAAAGTGAGCGTAGGTGGTCTTTCAAGTTG 541                                                              600
DHE.(cornell)    GATGTGAAATTTCCCGGCTTAACCGGGACGTGTCATTCAATACTGTTGGACTAGAGTACA
DHE.(stf).seq    GATGTGAAATTTCCCGGCTTAACCGGGACGTGTCATTCAATACTGTTGGACTAGAGTACA
DHE.(pl ).seq    GATGTGAAATTTCCCGGCTTAACCGGGACGTGTCATTCAATACTGTTGGACTAGAGTACA
DHE.(dll).seq    GATGTGAAATTTCCCGGCTTAACCGGGACGTGTCATTCAATACTGTTGGACTAGAGTACA
DHE.(dab).seq    GATGTGAAATTTCCCGGCTTAACCGGGACGAGTCATTCAATACTGTTGGACTAGAGTACA
DHE.(pin).seq    GATGTGAAATTTCCCGGCTTAACCGGGACGAGTCATTCAATACTGTTGGACTAGAGTACA 601                                                              660
DHE.(cornell)    GCAGGAGAAAACGGAATTCCCGGTGTAGTGGTAAAATGCGTAGATATCGGGAGGAACACC
DHE.(stf).seq    GCAGGAGAAAACGGAATTCCCGGTGTAGTGGTAAAATGCGTAGATATCGGGAGGAACACC
DHE.(pl ).seq    GCAGGAGAAAACGGAATTCCCGGTGTAGTGGTAAAATGCGTAGATATCGGGAGGAACACC
DHE.(dll).seq    GCAGGAGAAAACGGAATTCCCGGTGTAGTGGTAAAATGCGTAGATATCGGGAGGAACACC
DHE.(dab).seq    GCAGGAGAAAACGGAATTCCCGGTGTAGTGGTAAAATGCGTAGATATCGGGAGGAACACC
DHE.(pin).seq    GCAGGAGAAAACGGAATTCCCGGTGTAGTGGTAAAATGCGTAGATATCGGGAGGAACACC
```

FIG. 1D

```
                      661                                                         720
DHE.(cornell)         AGAGGCGAAGGCGGTTTTCTAGTTGTGTCACTGACACTGAGGCTCGAAAGCCTGGGGAGCG
DHE.(stf).seq         AGAGGCGAAGGCGGTTTTCTAGTTGTGTCACTGACACTGAGGCTCGAAAGCCTGGGGAGCG
DHE.(pl ).seq         AGAGGCGAAGGCGGTTTTCTAGTTGTGTCACTGACACTGAGGCTCGAAAGCGTGGGGAGCG
DHE.(dll).seq         AGAGGCGAAGGCGGTTTTCTAGTTGTGTCACTGACACTGAGGCTCGAAAGCGTGGGGAGCG
DHE.(dab).seq         AGAGGCGAAGGCGGTTTTCTAGTTGTGTCACTGACACTGAGGCTCGAAAGCGTGGGAGCG
DHE.(pin).seq         AGAGGCGAAGGCGGTTTTCTAGTTGTGTCACTGACACTGAGGCTCGAAAGCGTGGGAGCG 721                                                         780
DHE.(cornell)         AACAGAATTAGATACTCTGGTAGTCCACGCCCTTAAACTATGGACACTAGTAGGAGT
DHE.(stf).seq         AACAGAATTAGATACTCTGGTAGTCCACGCCCTTAAACTATGGACACTAGTAGGAGT
DHE.(pl ).seq         AACAGAATTAGATACTCTGGTAGTCCACGCCCTTAAACTATGGACACTAGTAGGAGT
DHE.(dll).seq         AACAGAATTAGATACTCTGGTAGTCCACGCCCTTAAACTATGGACACTAGTAGGAGT
DHE.(dab).seq         AACAGAATTAGATACTCTGGTAGTCCACGCCCTTAAACTATGGACACTAGTAGGAGT
DHE.(pin).seq         AACAGAATTAGATACTCTGGTAGTCCACGCCCTTAAACTATGGACACTAGTAGGAGT 781                                                         840
DHE.(cornell)         ATCGACCCTCTCTGTGCCGAAGCTAACGCTTTAAGTGTCCCGCCTGGGAGTACGGTCGC
DHE.(stf).seq         ATCGACCCTCTCTGTGCCGAAGCTAACGCTTTAAGTGTCCCGCCTGGGAGTACGGTCGC
DHE.(pl ).seq         ATCGACCCTCTCTGTGCCGAAGCTAACGCTYTAAGTGTCCCGCCTGGGAGTACGGTCGC
DHE.(dll).seq         ATCGACCCTCTCTGTGCCGAAGCTAACGCTTTAAGTGTCCCGCCTGGGAGTACGGTCGC
DHE.(dab).seq         ATCGACCCTCTCTGTGCCGAAGCTAACGCTTTAAGTGTCCCGCCTGGGAGTACGGTCGC
DHE.(pin).seq         ATCGACCCTCTCTGTGCCGAAGCTAACGCTTTAAGTGTCCCGCCTGGGAGTACGGTCGC
```

FIG. 1E

|            |      | 841                                                          | 900  |
|------------|------|--------------------------------------------------------------|------|
| DHE.(cornell).    | AAGGCTAAAACTCAAAGGAATTGACGGGGCCCGCACAAGCAGCGGAGCGTGTGGTTTAA |
| DHE.(stf).seq     | AAGGCTAAAACTCAAAGGAATTGACGGGGCCCGCACAAGCAGCGGAGCGTGTGGTTTAA |
| DHE.(pl).seq      | AAGGCTAAAACTCAAAGGAATTGACGGGGCCCGCACAAGCAGCGGAGCGTGTGGTTTAA |
| DHE.(dll).seq     | AAGGCTAAAACTCAAAGGAATTGACGGGGCCCGCACAAGCAGCGGAGCGTGTGGTTTAA |
| DHE.(dab).seq     | AAGGCTAAAACTCAAAGGAATTGACGGGGCCCCGCACAAGCAGCGGAGCGTGTGGTTTAA |
| DHE.(pin).seq     | AAGGCTAAAACTCAAAGGAATTGACGGGGCCCCGCACAAGCAGCGGAGCGTGTGGTTTAA |

|            |      | 901                                                          | 960  |
|------------|------|--------------------------------------------------------------|------|
| DHE.(cornell)     | TTCGATGCTACACGAAGAAC.TTACCAAGATTTGACATGCATGAAGTAGTGAACCGAAAG |
| DHE.(stf).seq     | TTCGATGCTACACGAAGAACGAAGAACCTTACCAAGATTTGACATGCATGAAGTAGTGAACCGAAAG |
| DHE.(pl).seq      | TTCGATGCTACACGAAGAACGAAGAACCTTACCAAGATTTGACATGCATGAAGTAGTGAACCGAAAG |
| DHE.(dll).seq     | TTCGATGCTACACGAAGAACGAAGAACCTTACCAAGATTTGACATGCATGAAGTAGTGAACTGAAAG |
| DHE.(dab).seq     | TTCGATGCTACACGAAGAACGAAGAACCTTACCAAGATTTGACATGCATGTAGTAGTGAACTGAAAG |
| DHE.(pin).seq     | TTCGATGCTACACGAAGAACGAAGAACCTTACCAAGATTTGACATGCATGTAGTAGTGAACTGAAAG |

|            |      | 961                                                          | 1020 |
|------------|------|--------------------------------------------------------------|------|
| DHE.(cornell)     | GGAAACGACCTGTTAAGTCAGGAGTTTGCACAGGTGCTGTGTCGTCAGCTCGTG |
| DHE.(stf).seq     | GGAAACGACCTGTTAAGTCAGGAGTTTGCACAGGTGCTGCATGGCTGTGTCGTCAGCTCGTG |
| DHE.(pl).seq      | GGAAACGACCTGTTAAGTCAGGAGTTTGCACAGGTGCTGCATGGCTGTGTCGTCAGCTCGTG |
| DHE.(dll).seq     | GGAAACGACCTGTTAAGTCAGGAGTTTGCACAGGTGCTGCATGGCTGTGTCGTCAGCTCGTG |
| DHE.(dab).seq     | GGGAACGACCTGTTAAGTCAGGAACTTGCACAGGTGCTGCATGGCTGTGTCGTCAGCTCGTG |
| DHE.(pin).seq     | GGGAACGACCTGTTAAGTCAGGAACTTGCACAGGTGCTGCATGGCTGTGTCGTCAGCTCGTG |

FIG. 1F

```
              1080
DHE.(cornell)  CCGTGAGGTGTGTTGGGTTAAGTCCTGCAACGAGCGCAACC..TTGTTGCTAGTTAAATTTTC
DHE.(stf).seq  CCGTGAGGTGTGTTTGGTTAAGTCCTGCAACGAGCGCAACCCTTGTTGCTAGTTAAATTTTC
DHE.(pl ).seq  CCGTGAGGTGTGTTTGGTTAAGTCCTGCAACGAGCGCAACCCTTGTTGCTAGTTAAATTTTC
DHE.(dll).seq  CCGTGAGGTGTTTGGTTAAGTCCTGCAACGAGCGCAACCCTTGTTGCTAGTTAAATTTTC
DHE.(dab).seq  CCGTGAGGTGTGTTTGGTTAAGTCCTGCAACGAGCGCAACCCTTGTTGCTAGTTAAATTTTC
DHE.(pin).seq  CCGTGAGGTGTGTTTGGTTAAGTCCTGCAACGAGCGCAACCCTTGTTGCTAGTTAAATTTTC 1140
DHE.(cornell)  TAGCGAGACTAGCCGAGACTGCCCCGCGAAACGGGAGGAAGGTGGGATGACGTCAAGTC
DHE.(stf).seq  TAGCGAG........ACTGCCCCGCGAAACGGGAGGAAGGTGGGATGACGTCAAGTC
DHE.(pl ).seq  TAGCGAG........ACTGCCCCGCGAAACGGGAGGAAGGTGGGATGACGTCAAGTC
DHE.(dll).seq  TAGCGAG........ACTGCCCCGCGAAACGGGAGGAAGGTGGGATGACGTCAAGTC
DHE.(dab).seq  TAGCGAG........ACTGCCCCGCGAAACGGGAGGAAGGTGGGATGACGTCAAGTC
DHE.(pin).seq  TAGCGAG........ACTGCCCCGCGAAACGGGAGGAAGGTGGGATGACGTCAAGTC 1200
DHE.(cornell)  AGCATGGCCTTTATATCTTGGGCTACACACACGCTACAATGGACAGAACAATAGGTTGCA
DHE.(stf).seq  AGCATGGCCTTTATATCTTGGGCTACACACACGCTACAATGACAGAACAATAGGTTGCA
DHE.(pl ).seq  AGCATGGCCTTTATATCTTGGGCTACACACACGCTACAATGACAGAACAATAGGTTGCA
DHE.(dll).seq  AGCATGGCCTTTATATCTTGGGCTACACACACGCTACAATGACAGAACAATAGGTTGCA
DHE.(dab).seq  AGCATGGCCTTTATATCTTGGGCTACACACACGCTACAATGACAGAACAATAGGTTGCA
DHE.(pin).seq  AGCATGGCCTTTATATCTTGGGCTACACACACGCTACAATGACAGAACAATAGGTTGCA
```

FIG. 1G

|  | 1201 | 1260 |
|---|---|---|
| DHE.(cornell) | ACAGTGTGAACTGGAGCTAATCCCAAAGCTGTCCTCAGTTCGGATTGCAGGCTGAAACC |  |
| DHE.(stf).seq | ACAGTGTGAACTGGAGCTAATCCTCAAAGCTGTCCTCAGTTCGGATTGCAGGCTGAAACC |  |
| DHE.(pl).seq | ACAGTGTGAACTGGAGCTAATCCCAAAGCTGTCCTCAGTTCGGATTGCAGGCTGAAACC |  |
| DHE.(dll).seq | ACAGTGTGAACTGGAGCTAATCCTCAAAGCTGTCCTCAGTTCGGATTGCAGGCTGAAACC |  |
| DHE.(dab).seq | ACAGTGTGAACTGGAGCTAATCCCCAAAGCTGTCCTCAGTTCGGATTGCAGGCTGAAACC |  |
| DHE.(pin).seq | ACAGTGTGAACTGGAGCTAATCCCAAAGCTGTCCTCAGTTCGGATTGCAGGCTGAAACC |  |

|  | 1261 | 1320 |
|---|---|---|
| DHE.(cornell) | CGCCTGCATGAAGTTGGAGTTGCTAGTAACCGCATATCAGCAAGGTGCCGGTGAATACGTT |  |
| DHE.(stf).seq | CGCCTGCATGAAGTTGGAGTTGCTAGTAACCGCATATCAGCAAGGTGCCGGTGAATACGTT |  |
| DHE.(pl).seq | CGCCTGCATGAAGTTGGAGTTGCTAGTAACCGCATATCAGCAAGGTGCCGGTGAATACGTT |  |
| DHE.(dll).seq | CGCCTGCATGAAGTTGGAGTTGCTAGTAACCGCATATCAGCAAGGTGCCGGTGAATACGTT |  |
| DHE.(dab).seq | CGCCTGCATGAAGTTGGAGTTGCTAGTAACCGCATATCAGCATGGTGCCGGTGAATACGTT |  |
| DHE.(pin).seq | CGCCTGCATGAAGTTGGAGTTGCTAGTAACCGCATATCAGCATGGTGCCGGTGAATACGTT |  |

|  | 1321 | 1380 |
|---|---|---|
| DHE.(cornell) | CTCGGGCCTTGTACACACCGCCCGTCACGTCATGANAGCCGGTAACACTTGAAGTCGATG |  |
| DHE.(stf).seq | CTCGGGCCTTGTACACACCGCCCGTCACGTCATGAAGCCGGTAACACTTGAAGTCGATG |  |
| DHE.(pl).seq | CTCGGGCCTTGTACACACCGCCCGTCACGTCATGAAAAGCCGGTAACACTTGAAGTCGATG |  |
| DHE.(dll).seq | CTCGGGCCTTGTACACACCGCCCGTCACGTCATGAAAAGCCGGTAACACTTGAAGTCGATG |  |
| DHE.(dab).seq | CTCGGGCCTTGTACACACCGCCCGTCACGTCATGAAAAGCCGGTAACACTTGAAGTCGATG |  |
| DHE.(pin).seq | CTCGGGCCTTGTACACACCGCCCGTCACGTCATGAAAAGCCGGTAACACTTGAAGTCGATG |  |

FIG. 1H

```
                1381                                                                        1440
DHE.(cornell)   TGCCAACCGCAAGGAGGCAGTCGCCCGAGGGTGGGACTGGTAATTGGGACGAAGTCGTAAC
DHE.(stf).seq   TGCCAACC....................................................
DHE.(pl ).seq   TGCCAACC....................................................
DHE.(dll).seq   TGCCAACC....................................................
DHE.(dab).seq   TGCCAACC....................................................
DHE.(pin).seq   TGCCAACC....................................................

1441  1446
DHE.(cornell)   AAGGTA (SEQ ID NO:7)
DHE.(stf).seq   ...... (SEQ ID NO:3)
DHE.(pl ).seq   ...... (SEQ ID NO:2)
DHE.(dll).seq   ...... (SEQ ID NO:6)
DHE.(dab).seq   ...... (SEQ ID NO:4)
DHE.(pin).seq   ...... (SEQ ID NO:5)
```

FIG. 11

The *Dehalococcoides sp.* alignment with *E. coli*

Name: E.coli.16S
Name: DHE.(cornell)
Name: DHE (stf).seq
Name: DHE.(pl ).seq
Name: DHE.(dab).seq
Name: DHE.(pin).seq
Name: DHE.(dll).seq
//

```
                    1                                                            60
E.coli.16S seq      AAATTGAAGAGTTTGATCATGGCTCAGATTGAACGCTGGCGGCAGGCCTAACACATGCAA
DHE.(cornell)       ............................GATGAACGCTAGCGGCGTGCCTTATGCATGCAA
DHE.(stf).seq       ............................GATGAACGCTAGCGGCGTGCCTTATGCATGCAA
DHE.(pl ).seq       ............................GATGAACGCTAGCGGCGTGCCTTATGCATGCAA
DHE.(dab).seq       ............................GATGAACGCTAGCGGCGTGCCTTATGCATGCAA
DHE.(pin).seq       ............................GATGAACGCTAGCGGCGTGCCTTATGCATGCAA
DHE.(dll).seq       ............................GATGAACGCTAGCGGCGTGCCTTATGCATGCAA 61                                                           120
E.coli.16S seq      GTCGAACGGTAACAGGAAGAAGCTTGCTTCTTTGCTGACGAGTGGCGGACGGGTGAGTAA
DHE.(cornell)       GTCGAACGGTCTTAAGCAA......TTAA........GAT.AGTGGCAAACGGGTGAGTAA
DHE.(stf).seq       GTCGAACGGTCTTAAGCAA......TTAA........GAT.AGTGGCAAACGGGTGAGTAA
DHE.(pl ).seq       GTCGAACGGTCTTAAGCAA......TTAA........GAT.AGTGGCAAACGGGTGAGTAA
DHE.(dab).seq       GTCGAACGGTCTTAAGCAA......TTAA........GAT.AGTGGCGAACGGGTGAGTAA
DHE.(pin).seq       GTCGAACGGTCTTAAGCAA......TTAA........GAT.AGTGGCGAACGGGTGAGTAA
DHE.(dll).seq       GTCGAACGGTCTTAAGCAA......TTAA........GAT AGTGGCAAACGGGTGAGTAA
```

FIG. 2A

```
                 121                                                              179
E.coli.16S seq   TGTCTGGGAAAC.TGCCTGATGAGGGGGGATAACTACTGGAAACGGTAGCTAATACCGCA
DHE.(cornell)    CGCGTAAGTAACCTACCTACCTCTAAGTGGGGGATAGCTTCGGGAAACTGAAGTAATACCGCA
DHE.(stf).seq    CGCGTAAGTAACCTACCTACCTCTAAGTGGGGGATAGCTTCGGGAAACTGAAGTAATACCGCA
DHE.(pl).seq     CGCGTAAGTAACCTACCTACCTCTAAGTGGGGGATAGCTTCGGGAAACTGAAGTAATACCGCA
DHE.(dab).seq    CGCGTAAGTAACCTACCTACCTCTAAGTGGGGGATAGCTTCGGGAAACTGAAGTAATACCGCA
DHE.(pin).seq    CGCGTAAGTAACCTACCTACCTCTAAGTGGGGGATAGCTTCGGGAAACTGAAGTAATACCGCA
DHE.(dll).seq    CGCGTAAGTAACCTACCTACCTCTAAGTGGGGGATAGCTTCGGGAAACTGAAGTAATACCGCA 180                                                              236
E.coli.16S seq   TAACGTCGCAAGACCAAAGAGGGGGACCTTCGGGCCTCTTGCCATCGCGATGTG...CCCA
DHE.(cornell)    TGTGATGGGCTGAC.ATAAGTCGGTTCATTAAAGCCGCAAGGTGCTTGGTGAGGGCTTG
DHE.(stf).seq    TGTGGTGGGCCGAC.ATAAGTTGGTTCACTAAAGCCGTAAGGTGCTTGGTGAGGGCTTG
DHE.(pl).seq     TGTGATGGGCTGAC.ATAAGTTGGTTCATTAAAGCCGCAAGGTGCTTGGTGAGGGCTTG
DHE.(dab).seq    TGTGGTGGGCCGAC.ATATGTTGGTTCACTAAAGCCGTAAGGCGCTTGGTGAGGGCTTG
DHE.(pin).seq    TGTGGTGGGCCGAC.ATATGTTGGTTCACTAAAGCCGTAAGGCGCTTGGTGAGGGCTTG
DHE.(dll).seq    TGTGGTGGGCCGAC.ATAAGTTGGTTCACTAAAGCCGTAAGGTGCTTGGTGAGGGCTTG 237                                                              295
E.coli.16S seq   GATGGGATTAGCTAGTAGGTGGGGTAACGGCTCACCTAGGCGACGATCCCTAGCT.GGTC
DHE.(cornell)    CGTCCGATTAGCTAGTTGGTGGGGTAATGTCTTACCAAGGCTTCGATCGGTAGCT.GGTC
DHE.(stf).seq    CGTCCGATTAGCTAGTTGGTGGGGTAACGGCCTACCAAGGCTTCGATCGGTAGCT.GGTC
DHE.(pl).seq     CGTCCGATTAGCTAGTTGGTGGGGTAATGCCTACCAAGGCCTACCAAGGCTTCGATCGGTAGCT.GGTC
DHE.(dab).seq    CGTCCGATTAGCTAGTTGGTGGGGTAATGCCTACCAAGGCCTACCAAGGCTTCGATCGGTAGCT.GGTC
DHE.(pin).seq    CGTCCGATTAGCTAGTTGGTGGGGTAATGCCTACCAAGGCCTACCAAGGCTTCGATCGGTAGCT.GGTC
DHE.(dll).seq    CGTCCGATTAGCTAGTTGGTGGGGTAACGGCCTACCAAGGCTTCGATCGGTAGCT.GGTC
```

FIG. 2B

```
                 296                                                            355
E.coli.16S seq   TGAGAGGATGACCAGCCACACTGAAACTGAGACACGGTCCAGACTCCTACGGGAGGCAGC
DHE.(cornell)    TGAGAGGATGATCAGCCACACTGGGACTGAGACACGGCCCAGACTCCTACGGGAGGCAGC
DHE.(stf).seq    TGAGAGGATGATCAGCCACACTGGGACTGAGACACGGCCCAGACTCCTACGGGAGGCAGC
DHE.(pl ).seq    TGAGAGGATGATCAGCCACACTGGGACTGAGACACGGCCCAGACTCCTACGGGAGGCAGC
DHE.(dab).seq    TGAGAGGATGATCAGCCACACTGGGACTGAGACACGGCCCAGACTCCTACGGGAGGCAGC
DHE.(pin).seq    TGAGAGGATGATCAGCCACACTGGGACTGAGACACGGCCCAGACTCCTACGGGAGGCAGC
DHE.(dll).seq    TGAGAGGATGATCAGCCACACTGGGACTGAGACACGGCCCAGACTCCTACGGGAGGCAGC 356                                                            415
E.coli.16S seq   AGTGGGGAATATTGCACAATGGGCGCAAGCCTGATGCAGCCATGCCGCGTGTATGAAGAA
DHE.(cornell)    AGCAAGGAATCTTGGGCAATGGGCGAAAGCCTGACCCAGCAACGCCGCGTGAGGGATGAA
DHE.(stf).seq    AGCAAGGAATCTTGGGCAATGGGCGAAAGCCTGACCCAGCAACGCCGCGTGAGGGATGAA
DHE.(pl ).seq    AGCAAGGAATCTTGGGCAATGGGCGAAAGCCTGACCCAGCAACGCCGCGTGAGGGATGAA
DHE.(dab).seq    AGCAAGGAATCTTGGGCAATGGGCGAAAGCCTGACCCAGCAACGCCGCGTGAGGGATGAA
DHE.(pin).seq    AGCAAGGAATCTTGGGCAATGGGCGAAAGCCTGACCCAGCAACGCCGCGTGAGGGATGAA
DHE.(dll).seq    AGCAAGGAATCTTGGGCAATGGGCGAAAGCCTGACCCAGCAACGCCGCGTGAGGGATGAA 416                                                            475
E.coli.16S seq   GGCCTTCGGGTTGTAAAGTACTTTCAGCGGGGAGGAAGGGAGTAAAGTTAATACCTTTGC
DHE.(cornell)    GGCTTTCGGGTTGTAAACCTCTTTTCACAGGGAAGAA............TAAT.......
DHE.(stf).seq    GGCTCTCGGGTTGTAAACCTCTTTTCACAGGAAGAA............TAAT.......
DHE.(pl ).seq    GGCTTTCGGGTTGTAAACCTCTTTTCACAGGGAAGAA............TAAT.......
DHE.(dab).seq    GGCTTTCGGGTTGTAAACCTCTTTTCATAGGGAAGAA............TAAT.......
DHE.(pin).seq    GGCTTTCGGGTTGTAAACCTCTTTTCATAGGGAAGAA............TAAT.......
DHE.(dll).seq    GGCTCTCGGGTTGTAAACCTCTTTTCACAGGGAAGAA............TAAT.......
```

FIG. 2C

```
              476                                                           535
E.coli.16S seq  TCATTGACGTTACCCGCAGAGAAGCACCGGCTAACTCCGTGCCAGCAGCCGCGGTAATA
DHE.(cornell)   ......GACGGTACCTGTGGAATAAGCTTCGGCTAACTACGTGCCAGCAGCCGCGGTAATA
DHE.(stf).seq   ......GACGGTACCTGTGGAATAAGCTTCGGCTAACTACGTGCCAGCAGCCGCGGTAATA
DHE.(pl).seq    ......GACGGTACCTGTGGAATAAGCTTCGGCTAACTACGTGCCAGCAGCCGCGGTAATA
DHE.(dab).seq   ......GACGGTACCTGTGGAATAAGCTTCGGCTAACTACGTGCCAGCAGCCGCGGTAATA
DHE.(pin).seq   ......GACGGTACCTGTGGAATAAGCTTCGGCTAACTACGTGCCAGCAGCCGCGGTAATA
DHE.(dll).seq   ......GACGGTACCTGTGGAATAAGCTTCGGCTAACTACGTGCCAGCAGCCGCGGTAATA 536                                                           594
E.coli.16S seq  CGGAGGGT.GCAAGCGTTAATCGGAATTACTGGGCGTAAAGCGCACGCAGGCGGTTTGTT
DHE.(cornell)   CGTAGGGAAGCAAGCGTTATCCGGATTTATTGGGCGTAAAGTGAGCGTAGGCGGTCTTTC
DHE.(stf).seq   CGTAGG..AAGCAAGCGTTATCCGGATTTATTGGGCGTAAAGTGAGCGTAGGCGGTCTTTC
DHE.(pl).seq    CGTAGG..AAGCAAGCGTTATCCGGATTTATTGGGCGTAAAGTGAGCGTAGGCGGTCTTTC
DHE.(dab).seq   CGTAGG..AAGCAAGCGTTATCCGGATTTATTGGGCGTAAAGTGAGCGTAGGCGGTCTTTC
DHE.(pin).seq   CGTAGG..AAGCAAGCGTTATCCGGATTTATTGGGCGTAAAGTGAGCGTAGGCGGTCTTTC
DHE.(dll).seq   CGTAGG..AAGCAAGCGTTATCCGGATTATTGGGCGTAAAGTGAGCGTAGGCGGTCTTTC 595                                                           654
E.coli.16S seq  AAGTCAGATGTGAAATCCCCGGGCTCAACCTGGGAACTGCATCTGATACTGGCAAGCTTG
DHE.(cornell)   AAGTTGGATGTGAAATTCCCGGCTTAACCGGACGTGTCATTCAATACTGTTGGACTAG
DHE.(stf).seq   AAGTTGGATGTGAAATTCCCGGCTTAACCGGACGTGTCATTCAATACTGTTGGACTAG
DHE.(pl).seq    AAGTTGGATGTGAAATTCCCGGCTTAACCGGACGTGTCATTCAATACTGTTGGACTAG
DHE.(dab).seq   AAGTTGGATGTGAAATTCCCGGCTTAACCGGACGAGTCATTCAATACTGTTGGACTAG
DHE.(pin).seq   AAGTTGGATGTGAAATTCCCGGCTTAACCGGACGAGTCATTCAATACTGTTGGACTAG
DHE.(dll).seq   AAGTTGGATGTGAAATTCCCGGCTTAACCGGACGTGTCATTCAATACTGTTGGACTAG
```

FIG. 2D

```
                       655                                                         714
E.coli.16S seq         AGTCTCGTAGAGGGGGGTAGAGAATTCCAGGTGTAGCGGTGAAATGCGTAGAGATCGGAGG
DHE.(cornell)          AGTACAGCAGGAGGAGAAACGGAATTCCCGGTGTAGTGGTGTAAAATGCGTAGATCGGGAGG
DHE.(stf).seq          AGTACAGCAGGAGGAGAAACGGAATTCCCGGTGTAGTGGTGTAAAATGCGTAGATATCGGGAGG
DHE.(pl ).seq          AGTACAGCAGGAGGAGAAACGGAATTCCCGGTGTAGTGGTAAAATGCGTAGATATCGGGAGG
DHE.(dab).seq          AGTACAGCAGGAGGAGAAACGGAATTCCCGGTGTAGTGGTAAAATGCGTAGATATCGGGAGG
DHE.(pin).seq          AGTACAGCAGGAGGAGAAACGGAATTCCCGGTGTAGTGGTAAAATGCGTAGATATCGGGAGG
DHE.(dll).seq          AGTACAGCAGGAGGAGAAACGGAATTCCCGGTGTAGTGGTAAAATGCGTAGATATCGGGAGG 715                                                         774
E.coli.16S seq         AATACCGGTGGCGAAGGCGGCCCCCTGGACGAAGACTGACGCTCAGGTGCGAAAGCGTGG
DHE.(cornell)          AACACCAGAGGCGAAGGCGGTTTTCTAGGTGTCACTGACACTGAGGCTCGAAAGCGTGG
DHE.(stf).seq          AACACCAGAGGCGAAGGCGGTTTTCTAGGTGTCACTGACACTGAGGCTCGAAAGCGTGG
DHE.(pl ).seq          AACACCAGAGGCGAAGGCGGTTTTCTAGGTGTCACTGACACTGAGGCTCGAAAGCGTGG
DHE.(dab).seq          AACACCAGAGGCGAAGGCGGTTTTCTAGGTGTCACTGACACTGAGGCTCGAAAGCGTGG
DHE.(pin).seq          AACACCAGAGGCGAAGGCGGTTTTCTAGGTTGTCACTGACACTGAGGCTCGAAAGCGTGG
DHE.(dll).seq          AACACCAGAGGCGAAGGCGGTTTTCTAGGTTGTCACTGACACTGAGGCTCGAAAGCGTGG 755                                                         834
E.coli.16S seq         GGAGCAAACAGGATTAGATACCCTGGTAGTCCACGCCGTAAACGATGTCGACTTGGAGGT
DHE.(cornell)          GGAGCGAACAGAATTAGATACTCTGGTAGTCCACGCCCTTAAACTATGGACACTAAGTATA
DHE.(stf).seq          GGAGCGAACAGAATTAGATACTCTGGTAGTCCACGCCCTTAAACTATGGACACTAAGTATA
DHE.(pl ).seq          GGAGCGAACAGAATTAGATACTCTGGTAGTCCACGCCCTTAAACTATGGACACTAGTATA
DHE.(dab).seq          GGAGCGAACAGAATTAGATACTCTGGTAGTCCACGCCCTTAAACTATGGACACTAGTATA
DHE.(pin).seq          GGAGCGAACAGAATTAGATACTCTGGTAGTCCACGCCCTTAAACTATGGACACTAGTATA
DHE.(dll).seq          GGAGCGAACAGAATTAGATACTCTGGTAGTCCACGCCCTTAAACTATGGACACTAGTATA
```

FIG. 2E

```
                835                                                                        893
E.coli.16S seq  TGTGCCCCTTGAGGCGTGCTT.CCGGAGCTAACGCGTTAAGTCGACCGCCTGGGGAGTAC
DHE.(cornell)   GGGAGTATCGACCCTCTCTGTGCCGAAGCTAACGCTTTAAGTGTCCCGCCTGGGGAGTAC
DHE.(stf).seq   GGGAGTATCGACCCTCTCTGTGCCGAAGCTAACGCTTTAAGTGTCCCGCCTGGGGAGTAC
DHE.(pl ).seq   GGGAGTATCGACCCTCTCTGTGCCGAAGCTAACGCTTTAAGTGTCCCGCCTGGGGAGTAC
DHE.(dab).seq   GGGAGTATCGACCCTCTCTGTGCCGAAGCTAACGCTTTAAGTGTCCCGCCTGGGGAGTAC
DHE.(pin).seq   GGGAGTATCGACCCTCTCTGTGCCGAAGCTAACGCTTTAAGTGTCCCGCCTGGGGAGTAC
DHE.(dll).seq   GGGAGTATCGACCCTCTCTGTGCCGAAGCTAACGCTTTAAGTGTCCCGCCTGGGGAGTAC 901                                                                        953
E.coli.16S seq  GGCCGCAAGGTTAAAACTCAAATGAATTGACGGGGCCCGCACAAGCGGTGGAGCATGTG
DHE.(cornell)   GGTCGCAAGGCTAAAACTCAAAGGAATTGACGGGGCCCGCACAAGCAGCGGAGCGTGTG
DHE.(stf).seq   GGTCGCAAGGCTAAAACTCAAAGGAATTGACGGGGCCCGCACAAGCAGCGGAGCGTGTG
DHE.(pl ).seq   GGTCGCAAGGCTAAAACTCAAAGGAATTGACGGGGCCCTTACAAGCAGCGGAGCGTGTG
DHE.(dab).seq   GGTCGCAAGGCTAAAACTCAAAGGAATTGACGGGGCCCGCACAAGCAGCGGAGCGTGTG
DHE.(pin).seq   GGTCGCAAGGCTAAAACTCAAAGGAATTGACGGGGCCCGCACAAGCAGCGGAGCGTGTG
DHE.(dll).seq   GGTCGCAAGGCTAAAACTCAAAGGAATTGACGGGGCCCGCACAAGCAGCGGAGCGTGTG 954                                                                        1011
E.coli.16S seq  GTTTAATTCGATGCAACGCGAAGAACCTTACCTGGTCTTGACATCCACGGA..AGTTTTC
DHE.(stf).seq   GTTTAATTCGATGCTACACGAAGAACCTTACCAAGATTTGACATGCATGAAGTAGTAGTGAAC
DHE.(pl ).seq   GTTTAATTCGATGCTACACGAAGAACCTTACCAAGATTTGACATGCATGAAGTAGTAGTGAAC
DHE.(dab).seq   GTTTAATTCGATGCTACACGAAGAACCTTACCAAGATTTGACATGCATGAAGTAGTAGTGAAC
DHE.(pin).seq   GTTTAATTCGATGCTACACGAAGAACCTTACCAAGATTTGACATGCATGAAGTAGTAGTGAAC
DHE.(dll).seq   GTTTAATTCGATGCTACACGAAGAACCTTACCAAGATTTGACATGCATGAAGTAGTAGTGAAC
```

FIG. 2F

```
                  1012                                                          1068
E.coli.16S seq    AGAGATGAGAATGTGCCTTCGGG..AACCGTGAG.ACAGGTGCTGCATGGCTGTCGTCAG
DHE.(cornell)     CGAAAGGGAAACGACCTGTTAAGTCAGGAGTTTGCACAGGTGCTGCATGGCTGTCGTCAG
DHE.(stf).seq     CGAAAGGGAAACGACCTGTTAAGTCAGGAGTTTGCACAGGTGCTGCATGGCTGTCGTCAG
DHE.(pl ).seq     CGAAAGGGAAACGACCTGTTAAGTCAGGAGTTTGCACAGGTGCTGCATGGCTGTGTCGTCAG
DHE.(dab).seq     TGAAAGGGAACGACCTGTTAAGTCAGGAACTTGCACAGGTGCTGCATGGCTGTCCTCAG
DHE.(pin).seq     TGAAAGGGAACGACCTGTTAAGTCAGGAACTTGCACAGGTGCTGCATGGCTGTCGTCAG
DHE.(dll).seq     CGAAAGGGAAACGACCTGTTAAGTCAGGAGTTTGCACAGGTGCTGCATGGCTGTCGTCAG 1069                                                          1128
E.coli.16S seq    CTCGTGTTGTGAAATGTTGGGTTAAGTCCCGCAACGAGCGCAACCCTTATCCTTTGTTGC
DHE.(cornell)     CTCGTGCCGTGAGGTGTTGGTTAAGTCCTGCAACGAGCGCAACC..TTGTTGCTAGTTA.
DHE.(stf).seq     CTCGTGCCGTGAGGTGTTGGTTAAGTCCTGCAACGAGCGCAACCCTTGTTGCTAGTTA.
DHE.(pl ).seq     CTCGTGCCGTGAGGTGTTTGGTTAAGTCCTGCAACGAGCGCAACCCTTGTTGCTAGTTA.
DHE.(dab).seq     CTCGTGCCGTGAGGTGTTTGGTTAAGTCCTGCAACGAGCGCAACCCTTGTTGCTAGTTA.
DHE.(pin).seq     CTCGTGCCGTGAGGTGTTTGGTTAAGTCCTGCAACGAGCGCAACCCTTGTTGCTAGTTA.
DHE.(dll).seq     CTCGTGCCGTGAGGTGTTTGGTTAAGTCCTGCAACGAGCGCAACCCTTGTTGCTAGTTA.

1129                                                          1187
E.coli.16S seq    CAGCGGTCCGGCCGGGAACTCAAAGGAGACTGCCAGTGATAAACTGG.AGGAAGGTGGGG
DHE.(cornell)     .AATTTTCTAGC.GAG.ACT..AGCGAGACTGCCC..CGCGAAACGGGGAGGAAGGTGGGG
DHE.(stf).seq     .AATTTTCTAGC.GAG............ACTGCCC..CGCGAAACGGGGAGGAAGGTGGGG
DHE.(pl ).seq     .AATTTTCTAGC.GAG............ACTGCCC..CGCGAAACGGGGAGGAAGGTGGGG
DHE.(dab).seq     .AATTTTCTAGC.GAG............ACTGCCC..CGCGAAACGGGGAGGAAGGTGGGG
DHE.(pin).seq     .AATTTTCTAGC.GAG............ACTGCCC..CGCGAAACGGGGAGGAAGGTGGGG
DHE.(dll).seq     .AATTTTCTAGC.GAG............ACTGCCC..CGCGAAACGGGGAGGAAGGTGGGG
```

FIG. 2G

```
                1247
E.coli.16S seq  ATGACGTCAAGTCATCATGGCCCTTACGACCAGGGCTACACACGTGCTACAATGGCGCAT
DHE.(cornell)   ATGACGTCAAGTCAGTCAGCATGGCCTTTATATCTTGGGCTACACACGCTACAATGACAGA
DHE.(stf).seq   ATGACGTCAAGTCAGTCAGCATGGCCTTTATATCTTGGGCTACACACACGCTACAATGACAGA
DHE.(pl ).seq   ATGACGTCAAGTCAGTCAGCATGGCCTTTATATCTTGGGCTACACACACGCTACAATGACAGA
DHE.(dab).seq   ATGACGTCAAGTCAGTCAGCATGGCCTTTATATCTTGGGCTACACACACGCTACAATGACAGA
DHE.(pin).seq   ATGACGTCAAGTCAGTCAGCATGGCCTTTATATCTTGGGCTACACACACGCTACAATGACAGA
DHE.(dll).seq   ATGACGTCAAGTCAGTCAGCATGGCCTTTATATCTTGGGCTACACACACGCTACAATGACAGA 1307
E.coli.16S seq  ACAAAGAGAAGCGACCTCGCGAGAGCAAGCGGACCTCATAAAGTGCGTCGTAGTCCGGAT
DHE.(cornell)   ACAATAGGTTGCAACAGTGTGAACTGTGAACTGGAGCTAATCCC.CAAAGCTGTCCTCAGTTCGGAT
DHE.(stf).seq   ACAATAGGTTGCAACAGTGTGAACTGTGAACTGGAGCTAATCCT.CAAAGCTGTCCTCAGTTCGGAT
DHE.(pl ).seq   ACAATAGGTTGCAACAGTGTGAACTGTGAACTGGAGCTAATCCC.CAAAGCTGTCCTCAGTTCGGAT
DHE.(dab).seq   ACAATAGGTTGCAACAGTGTGAACTGTGAACTGGAGCTAATCCC.CAAAGCTGTCCTCAGTTCGGAT
DHE.(pin).seq   ACAATAGGTTGCAACAGTGTGAACTGTGAACTGGAGCTAATCCC.CAAAGCTGTCCTCAGTTCGGAT
DHE.(dll).seq   ACAATAGGTTGCAACAGTGTGAACTGTGAACTGGAGCTAATCCT.CAAAGCTGTCCTCAGTTCGGAT 1367
E.coli.16S seq  TGGAGTCTGCAACTCGACTCCATGAAGTCGGAATCGCTAGTAATCGTGGATCAGAATGCC
DHE.(cornell)   TGCAGGCTGAAACCCGCCTGCATGAAGTTGGAGTTGCTAGTAACCGCATATCAGCAAGGT
DHE.(stf).seq   TGCAGGCTGAAACCCGCCTGCATGAAGTTGGAGTTGCTAGTAACCGCATATCAGCAAGGT
DHE.(pl ).seq   TGCAGGCTGAAACCCGCCTGCATGAAGTTGGAGTTGCTAGTAACCGCATATCAGCAAGGT
DHE.(dab).seq   TGCAGGCTGAAACCCGCCTGCATGAAGTTGGAGTTGCTAGTAACCGCATATCAGCATGGT
DHE.(pin).seq   TGCAGGCTGAAACCCGCCTGCATGAAGTTGGAGTTGCTAGTAACCGCATATCAGCATGGT
DHE.(dll).seq   TGCAGGCTGAAACCCGCCTGCATGAAGTTGGAGTTGCTAGTAACCGCATATCAGCAAGGT
```

FIG. 2H

```
                    1368                                                                1437
E.coli.16S seq   ACGGTGAATACGTTCCCGGGCCTTTGTACACACCGCCCGTCACACCATGGGAGTGGGTTGC
DHE.(cornell)    GCGGTGAATACGTTCTCGGGCCTTGTACACACCGCCCGTCACGTCATGAANAGCCGGTAAC
DHE.(stf).seq    GCGGTGAATACGTTCTCGGGCCTTGTACACACCGCCCGTCACGTCATGAAAGCCGGTAAC
DHE.(pl ).seq    GCGGTGAATACGTTCTCGGGCCTTGTACACACCGCCCGTCACGTCATGAAAGCCGGTAAC
DHE.(dab).seq    GCGGTGAATACGTTCTCGGGCCTTGTACACACCGCCCGTCACGTCATGAAAGCCGGTAAC
DHE.(pin).seq    GCGGTGAATACGTTCTCGGGCCTTGTACACACCGCCCGTCACGTCATGAAAGCCGGTAAC
DHE.(dll).seq    GCGGTGAATACGTTCTCGGGCCTTGTACACACCGCCCGTCACGTCATGAAAGCCGGTAAC 1438                                                                1487
E.coli.16S seq   AAAAGAAGTAGGTAGCTTAACCTTCGGGAGGGCGCTTACCACTTTGTGATTCATGACTGG
DHE.(cornell)    ACTTGAAGTCGATGTGCCAACCGCAAGGAGGCAGTCGCCGAGGGTGGGACTGGTAATTGG
DHE.(stf).seq    ACTTGAAGTCGATGTGCCAACC.......................................
DHE.(pl ).seq    ACTTGAAGTCGATGTGCCAACC.......................................
DHE.(dab).seq    ACTTGAAGTCGATGTGCCAACC.......................................
DHE.(pin).seq    ACTTGAAGTCGATGTGCCAACC.......................................
DHE.(dll).seq    ACTTGAAGTCGATGTGCCAACC.......................................

1488                                                        1542
E.coli.16S seq   GGTGAAGTCGTAACAAGGTAACCCGTAGGGGAACCTGCGGTTGGATCACCTCCTTA    (SEQ ID NO:33)
DHE.(cornell)    GACGAAGTCGTAACAAGGTA......................................    (SEQ ID NO:7)
DHE.(stf).seq    .........................................................    (SEQ ID NO:3)
DHE.(pl ).seq    .........................................................    (SEQ ID NO:2)
DHE.(dab).seq    .........................................................    (SEQ ID NO:4)
DHE.(pin).seq    .........................................................    (SEQ ID NO:5)
DHE.(dll).seq    .........................................................    (SEQ ID NO:6)
```

FIG. 21

NUCLEIC ACID FRAGMENTS FOR THE IDENTIFICATION OF DECHLORINATING BACTERIA

This application claims benefit of Provisional Application No. 60/129,511 filed Apr. 15, 1999.

FIELD OF THE INVENTION

The invention relates to the field of molecular biology and microbiology. More specifically, 16S rRNA regions of been identified and isolated from *Dehalococcoides ethenogenes* that enable the identification of dechlorinating bacterial strain. Probes and primers corresponding to the unique regions have been constructed to enable the rapid identification of the dechlorinators.

BACKGROUND

Groundwater pollution by halogenated, and particularly chlorinated solvents is a worldwide problem associated primarily with industrial sites where mishandling or improper disposal has brought these solvents in contact with the soil. The most common and problematic compounds are the chlorinated ethylenes (ethenes) such as tetra- tri- or di-chloroethylene. Carbon tetrachloride, chloroform and methylene chloride are also pervasive pollutants. The reasons for concern are basically threefold. First, most of these solvents are sparingly soluble in water and have the tendency to stick to soil particles. This results in tenacious underground plumes of solvent which cannot readily be removed by standard pump and treat technology (Biswas, N., et al., *Water Environ. Res.* 64, 170, 10, 1 (1992); Hutter, G. M., et. al., *Water Environ. Res.* 64, 69, (1992)). Second, the toxicology of many chlorinated solvents suggests that these compounds may be carcinogenic and damaging to specific organs such as the liver and Water, Washington, D.C.(1985); Vogel, T. M., *Environ. Sci. Technol.*, 21, 722, (1987)). Finally, under conditions found in many aquifers and subsurface environments, chlorinated ethylenes and methanes are very slow to be degraded biologically. The result of these factors is that chlorinated solvents are long-lived potentially hazardous groundwater pollutants.

Currently there are two approaches to in situ removal of organohalogen pollutants. The first approach is the standard "pump and treat" method where groundwater is pumped to the surface for physical stripping of the contaminant from the water. For chlorinated solvents this is more of a containment method than a remediation technology although given sufficient time (typically decades to centuries) this method may capture most of the pollutant. The other approach is biological in nature and utilizes microorganisms for the enzymatic transformation of the halogenated organics. The biological approach may utilize microorganisms indigenous to a particular site where the remediation process consists primarily of making additions to the contaminated site that enhance the growth of the desired microorganism. Alternatively, nonindigenous microorganisms may be introduced to a contaminated site with the necessary amendments needed for growth.

A number of organisms are known to dechlorinate persistent chlorinated pollutants. For example, *Dehalobacter restrictus* and *Dehalospirillium multivorans*, have been shown to partially dechlorinate chlorinated ethenes (Kochian et al., *Plant Mol Biol.* 46:237 (1995); Delhaize et al., *Plant Physiol.* 107:315 (1995)). Similarly, *Dehalococcoides ethenogenes* has been shown to effect the complete dechlorination of tetrachloroethene and trichloroethene to ethene [Freedman et al., *Appl. Environ. Microbiol.* 55:2144 (1989)] and Maymó-Gatell et al. (*Science*, 176:1568 (1997)) have isolated a *D. ethenogenes* strain that is capable of respiratory reductive dechlorination of tetrachloroethene directly to ethene with hydrogen as an electron donor. Analysis of the 16S rRNA of the Maymó-Gatell organism revealed a unique profile that may be used to identify organisms of similar reductive capabilities.

The first step in utilizing the dechlorinating properties of the above identified organisms is rapid and accurate identification. One method of identification involves the use of DNA probes (see for example in WO 89/06704, U.S. Pat. No. 4,851,330, and U.S. Pat. No. 5,574,145). Many such probes derive from the observation (see Woese, *Scientific American* 244 (6) 1981 for review) that parts of the 16S and 23s ribosomal RNA (rRNA) sequences vary in different species. This information was used initially for phylogenetic analyses but it has more recently been used for DNA probe-based methods for the identification of organisms. The utility of such a method is based on the conservation of nucleic acid sequence within the rRNA sequences.

Each of the cells of all life forms, except viruses, contains ribosomes and therefore ribosomal RNA. A ribosome contains three separate single strand RNA molecules, namely, a large molecule, a medium sized molecule, and a small molecule. The two larger rRNA molecules vary in size in different organisms. Ribosomal RNA is a direct gene product and is coded for by the rRNA gene. This DNA sequence is used as a template to synthesize rRNA molecules. A separate gene exists for each of the ribosomal RNA sub units. Multiple rRNA genes exist in most organisms, many higher organisms containing both nuclear and mitochondrial rRNA genes. Numerous ribosomes are present in all cells of all life forms. About 85–90 percent of the total RNA in a typical cell is rRNA. A bacteria such as *E. coli* contains about $10^4$ ribosomes per cell. Much of the sequences in rRNA highly conserved across broad evolutionary boundaries, however, certain regions are highly variable and may be used to make fine distinctions between species, sub-species and strains (U.S. Pat. No. 5,567,587).

The problem to be overcome therefore is to identify a unique 16S rDNA sequence in a bacteria capable of dechlorination of persistent chlorinated compounds for the identification and ultimate enhancement of that bacteria to remediated a contaminated site. Applicants have solved the stated problem by providing a set of nucleic acid sequences that are unique to various strains of *Dehalococcoides ethenogenes*.

SUMMARY OF THE INVENTION

The present invention provides an isolated 16S rDNA sequence indicative of a dechlorinating bacterial strain selected from the group consisting of: (a) SEQ ID NO:1, SEQ ID NO:2, SEQ ID NO:3, SEQ ID NO:4, SEQ ID NO:5, SEQ ID NO:6, SEQ ID NO:8, SEQ ID NO:30 and SEQ ID NO:34; (b) an isolated nucleic acid molecule that hybridizes with (a) under the following hybridization conditions: 0.1× SSC, 0.1% SDS at 65° C.; and (c) an isolated nucleic acid molecule that is completely complementary to (a) or (b).

The invention further provides primers and probes useful for the identification of new dechlorinating bacteria selected from the group consisting of: SEQ ID NOs:9–29 and SEQ ID Nos:35–60, and any sequences that hybridize under conditions of 0.1×SSC, 0.1% SDS at 65° C. to those primers and probes.

The invention additionally provides an isolated bacterial strain comprising any one of the sequences of the instant invention as set forth in SEQ ID NO: 1, SEQ ID NO:2, SEQ ID NO:3, SEQ ID NO:4, SEQ ID NO:5, SEQ ID NO:6 SEQ ID NO:8, SEQ ID NOs:9–29, SEQ ID NO:30, SEQ ID NO:34, and SEQ ID NOs:35–60 wherein said strain has the ability to dechlorinate chlorinated compounds.

The invention further provides a method for identifying a dechlorinating bacterial strain comprising: (i) extracting generic DNA from a cell suspected of being able to dechlorinate chlorinated compounds; (ii) probing the extracted genomic DNA with a probe derived from any one of the sequences instant invention as set forth in SEQ ID NO:1, SEQ ID NO:2, SEQ ID NO:3, SEQ ID NO:4, SEQ ID NO:5, SEQ ID NO:6 SEQ ID NO:8, SEQ ID NOs:9–29, SEQ ID NO:30, SEQ ID NO:34, and SEQ ID NOs:35–60 under suitable hybridization conditions, wherein the identification of a hybridizable nucleic acid fragment confirms the presence of a bacteria capable of dechlorinating chlorinated compounds.

Similarly the invention provides a method for identifying a dechlorinating bacterial strain comprising (i) extracting genomic DNA from a cell suspected of being able to dechlorinate chlorinated compounds; and (ii) amplifying the extracted genornic DNA with an oligonucleotide primer corresponding to a portion of any one of the sequences instant invention as set forth in SEQ ID NO:1, SEQ ID NO:2, SEQ ID NO:3, SEQ ID NO:4, SEQ ID NO:5, SEQ ID NO:6 SEQ ID NO:8, SEQ ID NOs:9–29, SEQ ID NO:30, SEQ ID NO:34, and SEQ ID NOs:35–60 such that amplification products are generated wherein the presence of amplification products confirms the presence of a dechlorinating bacterial strain.

The invention additionally provides a method for the dechlorination of chlorinated compounds comprising contacting a chlorinated compound with an isolated bacterial strain comprising any one of the DNA fragments as set forth in SEQ ID NO:1, SEQ ID NO:2, SEQ ID NO:3, SEQ ID NO:4, SEQ ID NO:5, SEQ ID NO:6 SEQ ID NO:8, SEQ ID NOs:9–29, SEQ ID NO:30, SEQ ID NO:34, and SEQ ID NOs:35–60 under conditions suitable for dechlorination to occur.

BRIEF DESCRIPTION OF THE DRAWINGS AND SEQUENCE LISTING

FIG. 1 (Panels A–I is an alignment of 16S rDNA sequence profile from *Dehalococcoides ethenogenes* DHE-195 as disclosed in Maymó-Gatell et al., *Science*, 176:1568 (1997), as compared with profiles generated for organisms isolated from a number of wastewater treatment sites.

FIG. 2 (Panals A–I) is a comparison of the instant dechlorinating 16S rDNA profiles with a 16S rDNA profile from *E. coli*.

Figure 3:
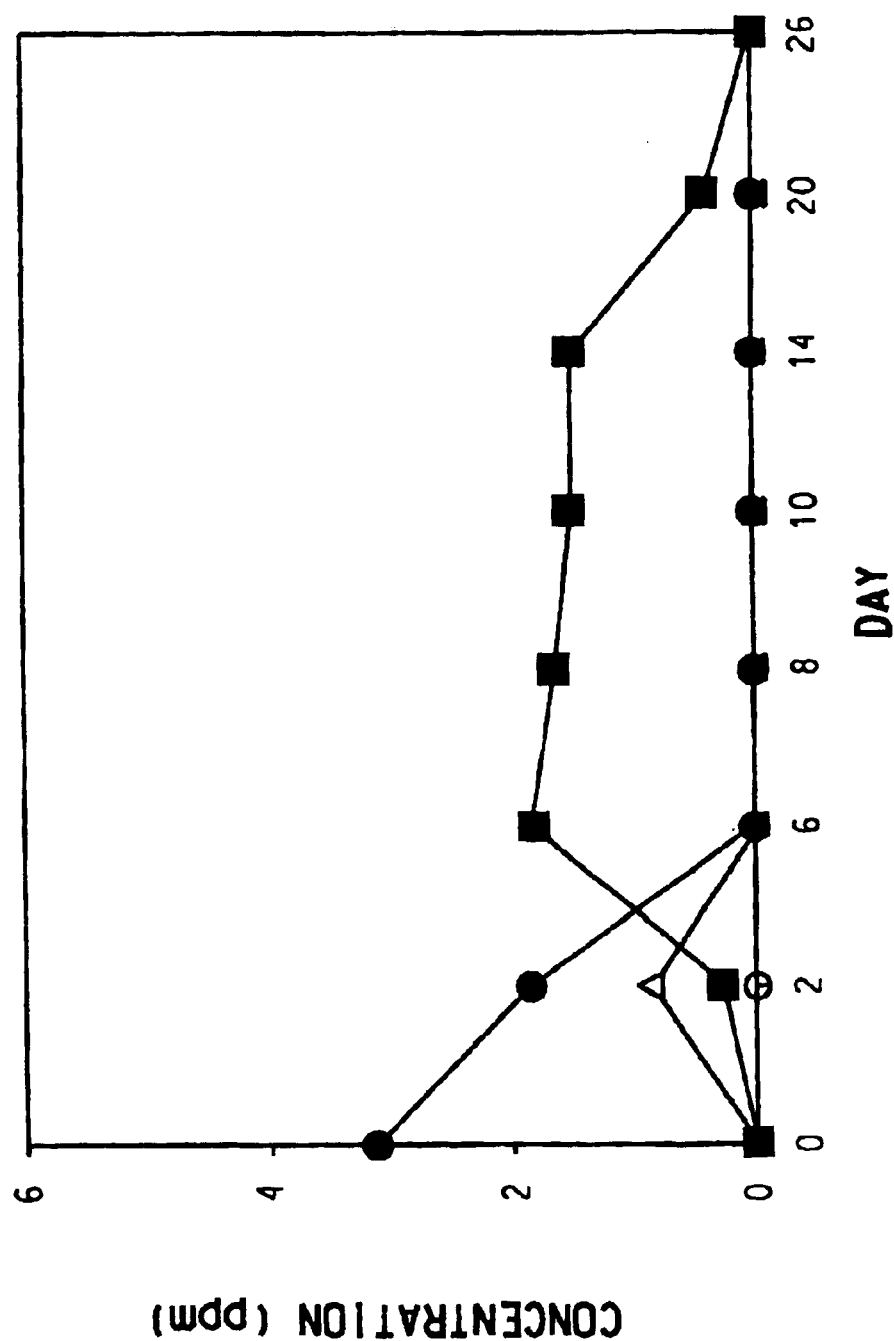
FIG. 3 is a graph illustrating the ability of a soil microcosm or culture developed from certain soils taken from a chloroethene contaminated site to dechlorinate trichloroethylene or perchloroethylene.

The following sequence descriptions and sequences listings attached hereto comply with the rules governing nucleotide and/or amino acid sequence disclosures in patent applications as set forth in 37 C.F.R. §1.821–1.825. The Sequence Descriptions contain the one letter code for nucleotide sequence characters and the three letter codes for amino acids as defined in conformity with the IUPAC-1YLJB standards described in *Nucleic Acids Research* 13:3021–3030 (1985) and in the *Biochemical Journal* 219 (No. 2):345–373 (1984) which are herein incorporated by reference. The symbols and format used for nucleotide and amino acid sequence data comply with the rules set forth in 37 C.F.R. §1.822.

SEQ ID NO:1 is a unique region of the *Dehalococcoides ethenogenes* 16S rDNA profile that is linked to dechlorinating activity.

SEQ ID NO:2 is the 16S rDNA profile of *Dehalococcoides ethenogenes* DHE-PL, isolated from soil surrounding in industrial site.

SEQ ID NO:3 is the 16S rDNA profile of *Dehalococcoides ethenogenes* DHE-STF, isolated from soil surrounding in industrial site.

SEQ ID NO:4 is the 16S rDNA profile of *Dehalococcoides ethenogenes* DHE-DAB, isolated from soil surrounding in industrial site.

SEQ ID NO:5 is the 16S rDNA profile of *Dehalococcoides enthenogenes* DHE-PIN, isolated from soil surrounding in industrial site.

SEQ ID NO:6 is the 16S rDNA profile of *Dehalococcoides enthenogenes* DHE-DLL, isolated from soil surrounding in industrial site.

SEQ ID NO:7 is the 16S rDNA profile of *Dehalococcoides enthenogenes* DHE-195 as reported in Maymó-Gatell et al. (*Science*, 176:1568 (1997)), Genbank AF004928.

SEQ ID NO:8 is the consensus sequence derived from DHE-PL, DHE-STF, DHE-DAB, DHE-PIN, and DHE-DLL at bases E180–E226.

SEQ ID NO:9–29 are primers derived from the 16S rDNA profile, useful in the identification of dechlorinating bacteria.

SEQ ID NO:30 is the consensus sequence derived from DHE-PL, DHE-STF, DHE-DAB, DHE-PIN, and DHE-DLL at bases E1001–E1047.

SEQ ID NO:31 is the base sequence in the region of the consensus 16S rDNA profile from where the diagnostic sequence is derived.

SEQ ID NO:32 is the base sequence in the region of the DHE-195 16S rDNA profile from where the diagnostic sequence is derived.

SEQ ID NO:33 is the *E. coli* reference 16S rDNA sequence.

SEQ ID NO:34 is a unique region of the *Dehalococcoides enthenogenes* 16S rDNA profile that is linked to dechlorinating activity.

SEQ ID NO:'s 35–60 are probes designed from unique regions of the *Dehalococcoides enthenogenes* 16S rDNA profile that are linked to dechlorinating activity.

DETAILED DESCRIPTION OF THE INVENTION

The present invention provides unique 16S rDNA sequence profiles derived from *Dehalococcoides enthenogenes* (DHE). *D. ethenogenes* is known for its ability to degrade persistent chlorinated pollutants. The instant sequence profiles may be used to identify and subtype bacteria with similar metabolic pathways. One sequence (SEQ ID NO:1), beginning at base E1146, has been identified in all DHE's isolated from contaminated soils and is strongly linked to the ability of these organisms to degrade chlorinated organics. Similarly, a longer sequence has been identified (SEQ ID NO:34), beginning at base E1112 and extending to base E1175, which contains SEQ ID NO:1, but is itself unique is diagnostic for the ability of these organisms to degrade chlorinated organics. Additionally, a stretch of nucleic acids ranging between E180 and E226, corresponding to SEQ ID NO:8, may be used to identify dechlorinators as well as for genetic sub-typing of species.

In this disclosure, a number of terms and abbreviations are used. The following definitions are provided.

The term "*Dehalococcoides enthenogenes*" will be abbreviated "DHE".

The term "DHE-195" or "DHE (cornell)" will refer to the strains of *Dehalococcoides ethenogenes* isolated and characterized by Maymó-Gatell et al. (*Science*, 176:1568 (1997)).

The terms "DHE-PL, DHE-STF, DHR-DAB, DHE-DLL and DHE-PIN" will refer to strains of Dehalococcoides sp. containing the instant dechlorinating 16S rDNA profile.

The term "dechlorinating bacteria" refers to any bacterial species or strain that has the ability to remove at least one chlorine atom from a chlorinated organic compound. Dechlorinating bacteria may have the ability to grow on chlorinated organics as a sole carbon source, or may prefer degradation using an alternate energy source.

The term "chlorinated compounds" will mean any straight chain or ring containing organic compound which contains at least one chlorine atom.

Trichloroethylene will be abbreviated "TCE".

Perchloroethylene will be abbreviated "PCE".

The term "16S rDNA" will refer to the DNA encoding ribosomal RNA found within bacterial cells.

The term "16S rDNA profile" will refer to the specific DNA sequence of the rDNA gene in any particular organism. For the purposes of the present invention the 16S rDNA profiles for DHE-195, DHE-PL, DHE-STF, DHE-DAB, DHE-DLL and DHE-PIN are illustrated in FIGS. 1 and 2.

The term "signature sequence" or "signature sequence region" or "signature groups" will refer to those short sequences in the 16S gene or rRNA molecule which are unique to a certain group or groups of organisms. These sequences can be used to define domains, group, subdivisions genera or species of an organism.

The term "consensus sequence" as used herein, as it relates to the alignment of a given set of sequences, will be defined as the sequence of the set of bases where a designated base is the one that occurs most often at each position in the 16S sequence.

The term "reference sequence" as used herein, as it relates to the alignment of a given set of sequences, will be defined as the particular 16S sequence to which the bases at each position of an alignment of 16S sequences are compared. The reference sequence used herein was an *E. coli* 16S rDNA sequence. Bases identified in the reference sequence that correlate to corresponding bases in a 16S rDNA profiled are assigned an "E number". Thus, the base labeled E-27 on the reference sequence corresponds to base 1 of the 16S rDNA profile of DHE-195 and E-107 corresponds to base 66 of DHE-195. The complete correlation is given in Table 2.

The term "dechlorinating 16S rDNA profile" will refer to a 16S rDNA profile containing the diagnostic sequence as set forth in SEQ ID NO:1.

The term "diagnostic sequence" will refer to the sequences as set forth in SEQ ID NO:1 or SEQ ID NO:34 which are indicative of dechlorinating activity.

The letters "A", "G", "T", "C" when referred to in the context of nucleic acids will mean the purine bases Adenine ($C_5H_5N_5$), Guanine ($C_5H_5N_5O$) and the pyrimidine bases Thymine ($C_5H_6N_2O_2$) and Cytosine ($C_4H_5N_3O$) respectively.

"Gene" refers to a nucleic acid fragment that expresses a specific protein, including regulatory sequences preceding (5' non-coding sequences) and following (3' non-coding sequences) the coding sequence.

The term "nucleic acid fragment" will refer to a polymer of RNA or DNA that is single- or double-stranded, optionally containing synthetic, non-natural or altered nucleotide bases. A nucleic acid fragment in the form of a polymer of DNA may be comprised of one or more segments of cDNA, genomic DNA or synthetic DNA.

The term "oligonucleotide" refers to primers, probes, oligomer fragments to be detected, labeled-replication blocking probes, oligomer controls, and shall be generic to polydeoxyribonucleotides (containing 2-deoxy-D-ribose), to polyribonucleotides (containing D-ribose) and to any polynucleotide which is an N glycoside of a purine or pyrimidine base (nucleotide), or modified purine or pyrimidine base. Also included in the definition of "oligonucleotide" are nucleic acid analogs (e.g., peptide nucleic acids) and those that have been structurally modified (e.g., phosphorothioate linkages). There is no intended distinction between the length of a "nucleic acid", "polynucleotide" or an "oligonucleotide".

The term "primer" refers to an oligonucleotide (synthetic or occurring naturally), which is capable of acting as a point of initiation of nucleic acid synthesis or replication along a complementary strand when placed under conditions in which synthesis of a complementary stand is catalyzed by a polymerase.

The term "probe" refers to an oligonucleotide (synthetic or occurring naturally), that is significantly complementary to a "fragment" and forms a duplexed structure by hybridization with at least one strand of the fragment.

The term "replication inhibitor moiety" refers to any atom, molecule or chemical group that is attached to the 3' terminal hydroxyl group of an oligonucleotide that will block the initiation of chain extension for replication of a nucleic acid strand. Examples are (but not limited to) 3'-deoxynucleotides (e.g., cordycepin), dideoxynucleotides, phosphate, ligands (e.g., biotin, dinitrophenol), reporter molecules (e.g., fluorescein, rhodamine), carbon chains (e.g., propanol), a mismatched nucleotide or polynucleotide, or peptide nucleic acid units.

The term "non-participatory" will refer to the lack of participation of a probe or primer in a reaction for the amplification of a nucleic acid molecule. Specifically a non-participatory probe or primer is one will not serve as a substrate for, or be extended by, a DNA or RNA polymerase. A "non-participatory probe" is inherently incapable of being chain extended by a polymerase. It may or may not have replication inhibitor moiety.

The term "complementary" is used to describe the relationship between nucleotide bases that are hybridizable to one another. For example, with respect to DNA, adenosine is complementary to thymine and cytosine is complementary to guanine.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength. Hybridization and washing conditions are well known and exemplified in Sambrook, J., Fritsch, E. F. and Maniatis, T. *Molecular Cloning: A Laboratory Manual*, Second Edition, Cold Spring Harbor Laboratory Press, Cold Spring Harbor (1989), particularly Chapter 11 and Table 11.1 therein (entirely incorporated herein by reference). The conditions of temperature and ionic strength determine the "stringency" of the hybridization. For preliminary screening for homologous nucleic acids, low stringency hybridization conditions, corresponding to a Tm of 55°, can be used, e.g., 5×SSC, 0.1% SDS, 0.25% milk, and no formamide; or 30% formamide, 5×SSC, 0.5% SDS. Moderate stringency hybridization conditions correspond to a higher Tm, e.g., 40% formamide, with 5× or 6×SSC.

Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of Tm for hybrids of nucleic acids having those sequences. The relative stability (corresponding to higher Tm) of nucleic acid hybridizations decreases in the following order: RNA:RNA, DNA:RNA, DNA:DNA. For hybrids of greater than 100 nucleotides in length, equations for calculating Tm have been derived (see Sambrook et al., supra, 9.50–9.51, hereby incorporated by reference). For hybridizations with shorter nucleic acids, i.e., oligonucleotides, the position of mismatches becomes more important, and the length of the oligonucleotide determines its specificity (see Sambrook et al., supra, 11.7–11.8, hereby incorporated by reference). In one embodiment the length for a hybridizable nucleic acid is at least about 10 nucleotides. Preferable a minimum length for a hybridizable nucleic acid is at least about 15 contiguous nucleotides; more preferably at least about 20 contiguous nucleotides; and most preferably the length is at least 30 contiguous nucleotides. Thus, where a "probe" or "primer" is "derived from" or corresponds to a "portion" of a nucleic acid fragment, the probe or primer or portion will preferably be at least about 15 contiguous nucleotides; more preferably at least about 20 contiguous nucleotides; and most preferably the length is at least 30 contiguous nucleotides of the fragment from which it is derived. Furthermore, the skilled artisan will recognize that the temperature and wash solution salt concentration may be adjusted as necessary according to factors such as length of the probe.

The term "amplification product" refers to portions of nucleic acid fragments that are produced during a primer directed amplification reaction. Typical methods of primer directed amplification include polymerase chain reaction (PCR), ligase chain reaction (LCR) or Strand displacement Amplification (SDA). If PCR methodology is selected, the replication composition would include for example, nucleotide triphosphates, two primers with appropriate sequences, DNA or RNA polymerase and proteins. These reagents and details describing procedures for their use in amplifying nucleic acids are provided in U.S. Pat. No. 4,683,202 (1987, Mullis, et al.) and U.S. Pat. No. 4,683,195 (1986, Mullis, et al.). If LCR methodology is selected, then the nucleic acid replication compositions would comprise, for example, a thermostable ligase, e.g., *T. aquaticus* ligase, two sets of adjacent oligonucleotides wherein one member of each set is complementary to each of the target strands, Tris HCl buffer, KCl, EDTA, NAD, dithiothreitol and salmon sperm DNA. See, for example, Tabor et al., *Proc. Acad. Sci. U.S.A.*, 82, 1074–1078 (1985)).

The term "sequence analysis software" refers to any computer algorithm or software program that is useful for the analysis of nucleotide or amino acid sequences. "Sequence analysis software" may be commercially available or independently developed. Typical sequence analysis software will include but is not limited to the GCG suite of programs (Wisconsin Package Version 9.0, Genetics Computer Group (GCG), Madison, Wis.), BLASTP, BLASTN, BLASTX (Altschul et al., *J Mol. Biol.* 215:403–410 (1990), and DNASTAR (DNASTAR, Inc., 1228 S. Park St. Madison, Wis. 53715 USA). Within the context of this application it will be understood that where sequence analysis software is used for analysis, that the results of the analysis will be based on the "default values" of the program referenced, unless otherwise specified. As used herein "default vales" will mean any set of values or parameters which originally load with the software when first initialized.

Standard recombinant DNA and molecular cloning techniques used here are well known in the art and are described by Sambrook, J., Fritsch, E. F. and Maniatis, T., *Molecular Cloning: A Laboratory Manual*, Second Edition, Cold Spring Harbor Laboratory Press, Cold Spring Harbor, N.Y. (1989) (hereinafter "Maniatis"); and by Silhavy, T. J., Bennan, M. L. and Enquist, L. W., *Experiments with Gene Fusions*, Cold Spring Harbor Laboratory Cold Press Spring Harbor, N.Y. (1984); and by Ausubel, F. M. et al., *Current Protocols in Molecular Biology*, published by Greene Publishing Assoc. and Wiley-Interscience (1987).

The present invention relates to unique 16S rDNA sequences which have been isolated from the bacteria very similar if not related to *Dehalococcoides enthenogenes*, which are associated with the ability of this bacteria to dechlorinate chlorinated organic compounds. The sequences were isolated from bacteria found in soil samples of various industrial sites that have been shown to contain bacteria that have the ability to dechlorinate chlorinated compounds. The sequences are useful for the identification new dechlorinating bacteria, as well as for sub-typing strains of *Dehalococcoides ethenogenes*.

Dechlorinating bacteria were isolated from the aquifer soil taken from around industrial sites by means well known in the art. Samples were maintained under anaerobic conditions and cultured in a suitable medium for the growth of anaerobic soil bacteria. Such culture procedures and media are common and well known in the art and are described in *Manual of Methods for General Bacteriology* (Phillipp Gerhardt, R. G. E. Murray, Ralph N. Costilow, Eugene W. Nester, Willis A. Wood, Noel R. Krieg and G. Briggs Phillips, eds), American Society for Microbiology, Washington, D.C. (1994)) or by Thomas D. Brock in *Biotechnology: A Textbook of Industrial Microbiology*, Second Edition, Sinauer Associates, Inc., Sunderland, Mass. (1989).

In order to enrich the cultured soil samples for dechlorinating bacteria, the samples were contacted with a low level of chlorinated organic compound. A number of chlorinated compounds are suitable for this purpose, including, but not limited to carbontetrachloride, tetrachloroethene, chloroform, dichloromethane, trichloroethene, dichloroethylene, vinyl chloride, and chloroaromatics, where chlorinated ethenes are preferred and TCE and PCE are preferred. Incubation proceeded for about six months, and cultures were analyzed periodically for the disappearance of the chlorinated organic and the appearance of degradation products. Cultures demonstrating the ability to degrade chlorinated organics, were selected for further analysis.

Bacteria from dechlorinating cultures were removed by standard methods and total chromosomal DNA was isolated from the microorganisms through a bead mill homogenization procedure. A fragment of the 16S rRNA gene was amplified from the genomic DNA extract by PCR using 16S rDNA primers specific for dechlorinating microbes. The 16S rDNA PCR product was cloned and sequenced to confirm its identity (M. I. More et al. 1994. *Appl. Environ. Aicrobiol.*, 60, 1572–1580). Each raw 16S sequences obtained were assembled into a contig, and a consensus was manually constructed using Seqman II in DNAstar (DNAstar, Inc., Madison, Wis.). For each test sequence, a Pearson and Lipman similarity search was performed using the FASTA program in GCG (Wisconsin Package Version 9.0, Genetics Computer Group, Madison, Wis.). The nearest organism in similarity in 16S rRNA sequence to the test sequence was used as the nearest match for identification. Those 16S DNA gene sequences that were identified to be similar to the dechlorinating bacteria, *Dehalococcoides enthenogenes* DHE-195 (GenBank Accession No. AF004928), were aligned with selected 16s rRNA sequences extracted from the Ribosomal Database Project (Michigan State University) that were a representation of the major microorganism domains, Bacteria and Archeae in the Universal Phylogenetic Tree of Life. The sequences were aligned using MegAlign in DNAstar, using the default software parameters. From this alignment probable region for signature sequences were mapped. Then sequences from each region were tested against the Ribosomal Database (RDB) for unique sequences that could be signature sequences and utilized as PCR primes or detection probes.

Within the 16S rDNA profile defined by the comparison of the isolated dechlorinators, (see FIGS. 1 and 2) four signature regions showed considerable variation from the known sequences. Those regions were defined as extending from E1146 to E1156 (SEQ ID NO:1), from E180 to E227 (SEQ ID NO:8), and from E1001 to E1047 (SEQ ID NO:30). A fourth sequence, SEQ ID NO:34, which contains SEQ ID NO:1 is also unique and may be used to definitely identify these organisms. All of the dechlorinating isolates of the present invention contained the sequence as set forth in SEQ ID NO:1 or SEQ ID NO:34 which are conspicuously absent from the sequence known in the art (Maymó-Gatell et al. (*Science*, 176:1568 (1997)). SEQ ID NO:34 extends from E1112 to E1175 and contains SEQ ID NO:1 as shown by the double unlined portion below.

```
E1114    E1118                        E1168
  |        |                            |
AACCCTTGTTGCTAGTTAAATTTTCTAGCGAGACTGCCCCGCGAAACGG (SEQ ID NO:34)
```

Although a region similar to that defined by SEQ ID NO:8 is found in the literature sequence, there are significant variations at positions, E184, E190, E197, E200, E207, E216, and E221 as shown below.

```
              E184 E190   E197 E200    E207    E216 E221
                |    |      |    |       |       |    |
              TGTGRTGGGCY GACATAWGTY GGTTCAYTAA AGCCGYAAGGYGC TTG (SEQ ID NO:8)
```

With in the context the present invention Applicants have discovered that within the signature region defined by SEQ ID NO:8 above, the R at position E184 may be A|G, the Y at position E190 may be C/T, the W at position E197 may be A/T, and the Y's at position E200, E207, E216, and E221 may be T/C.

Similarly the region defined by SEQ ID NO:30 is also found in the literature but contains significant variations at positions, E1003, E1012, E1020, E1039, and E1040 as shown below.

```
         E1003            E1012  E1020                   E1039
           |                |      |                       |
         TGWAGTAGTGAACMGAAAGGGRAACGACCTGTTAAGTCAGGARMTTGCACA (SEQ ID NO:30)
                                                            |
                                                          E1040
```

As with SEQ ID NO:8, Applicants have discovered that within the signature region defined by SEQ ID NO:30 above, the W at position E1003 may be A/T at position E1012 the M may be A/C, at position E1020 the R may be A/G, at position E1039 the R may be A/G and, at position E1040 the M may be A/C.

Likewise, if the entire 16S rDNA profile is examined, it is seen that there are significant single base differences throughout the entire profile (FIGS. 1 and 2). These differences are illustrated in tabular form in Table 2. Accordingly a 16S rDNA profile sequence, having the following bases substitutions taken independently or together will be diagnostic for dechlorinating bacteria: E107=G, base E184=G, base E190=C, E197=T, E200=T, E207=C, E216=T, E221= C, E264=C, E267=C, E291=T, E333=C, E420=C, E444=T, E631=A, E829=A, E933=T, E934=T, E980=C, E1003=T, E1012=T, E1020=G, E1039=A, E1040=C, E1087=T, E1114=C, E1284=T, E1364=T and E1427=A Assay Methods The instant sequences may be used in a variety of formats for the detection of dechlorinating bacteria. The two most convenient formats will rely on methods of nucleic acid hybridization or priner directed amplification methods such as PCR Nucleic Acid Hybridization Methods The basic components of a nucleic acid hybridization test include a probe, a sample suspected of containing a dechlorinating bacteria and a specific hybridization method. As noted above, probes of the present invention are single strand nucleic acid sequence which is complementary to the nucleic acid sequences to be detected. Probes are "hybridizable" to the nucleic acid sequence to be detected. The probe length can vary from 5 bases to tens of thousands of bases, and will depend upon the specific test to be done. Only part of the probe molecule need be complementary to the nucleic acid sequence to be detected. In addition, the complementarity between the probe and the target sequence need not be perfect. Hybridization does occur between imperfectly complementary molecules with the result that a certain fraction of the bases in the hybridized region are not paired with the proper complementary base. A probe may be composed of either RNA or DNA. The form of the nucleic acid probe may be a marked single strand molecule of just one polarity or marked single strand molecule having both polarities present. The form of the probe, like its length, will be determined by the type of hybridization test to be done.

The sample may or may not contain the organism of interest. The sample may take a variety of forms, including liquid such as water, or solid such as dust, or soil. The sample nucleic acid must be made available to contact the probe before any hybridization of probe and target molecule can occur. Thus the organism's RNA must be free from the cell and placed under the proper conditions before hybridization can occur. Methods of in solution hybridization necessitate the purification of the RNA in order to be able to obtain hybridization of the sample rRNA with the probe. This has meant that to utilize the in solution method for detecting target sequences in a sample, the nucleic acids of the sample must first be purified to eliminate protein, lipids, and other cell components, and then contacted with the probe under hybridization conditions. Method for the purification of the sample nucleic acid are common and well known in the art (Maniatis, supra).

Similarly, hybridization methods are well defined. Typically the probe and sample must be mixed under conditions which will permit nucleic acid hybridization. This involves contacting the probe and sample in the presence of an inorganic or organic salt under the proper concentration and temperature conditions. The probe and sample nucleic acids must be in contact for a long enough time that any possible hybridization between the probe and sample nucleic acid may occur. The concentration of probe or target in the mixture will determine the time necessary for hybridization to occur. The higher the probe or target concentration the shorter the hybridization incubation time needed.

In one embodiment, hybridization assays may be conducted directly on bacterial lysates, without the need to extract the nucleic acids. This eliminates several steps from the sample-handling process and speeds up the assay. To perform such assays on crude cell lysates, a chaotropic agent is typically added to the cell lysates prepared as described above. The chaotropic agent stabilizes nucleic acids by inhibiting nuclease activity. Furthermore, the chaotropic agent allows sensitive and stringent hybridization of short oligonucleotide probes to RNA at room temperature [Van Ness and Chen (1991) *Nucl. Acids Res.* 19:5143–5151]. Suitable chaotropic agents include guanidinium chloride, guanidinium thiocyanate, sodium thiocyanate, lithium tetrachloroacetate, sodium perchlorate, rubidium tetrachioroacetate, potassium iodide, and cesium trifluoroacetate, among others. Typically, the chaotropic agent will be present at a final concentration of about 3M. If desired, one can add formamide to the hybridization mixture, typically 30–50% (v/v).

Alternatively, one can purify the rRNA prior to probe hybridization. A variety of methods are known to one of skill in the art (e.g., phenol-chloroform extraction, IsoQuick extraction (MicroProbe Corp., Bothell, Wash.), and others). Pre-hybridization purification is particularly useful for standard filter hybridization assays. Furthermore, purification facilitates measures to increase the assay sensitivity by incorporating in vitro RNA amplification methods such as self-sustained sequence replication (see for example Fahy et al. (1991) in *PCR Methods and Applications*, Cold Spring Harbor Laboratory Press, pp. 25–33) or reverse tnanscriptase PCR (Kawasaki (1990) in PCR *Protocols: A Guide to Methods and Applications*, M. A. Innis et al., eds., pp. 21–27). One can obtain amplified rRNA by using in vitro RNA amplification techniques as described in Fahy et al., supra.; Kawasaki, supra. The exact procedure used is not crucial, provided that it does not amplify significant amounts of DNA, which would tend to obscure results.

Once the pre-rRNA is released from the cells, it can be detected by any of a variety of methods. The method of rRNA detection is not crucial to the invention. However, the most useful embodiments have at least some of characteristics of speed, convenience, sensitivity, and specificity. Direct DNA probe analysis is suitable, as is an in vitro RNA amplification method, such as 3SR, that employs labeled primers.

Various hybridization solutions can be employed. Typically, these comprise from about 20 to 60% volume, preferably 30%, of a polar organic solvent A common hybridization solution employs about 30–50% v/v formamide, about 0.15 to 1M sodium chloride, about 0.05 to 0.1M buffers, such as sodium citrate, Tris-HCl, PIPES or HEPES (pH range about 6–9), about 0.05 to 0.2% detergent, such as sodium dodecylsulfate, or between 0.5–20 mM EDTA, FICOLL (Pharmacia Inc.) (about 300–500 kilodaltons), polyvinylpyrrolidone (about 250–500 kdal), and serum albumin. Also included in the typical hybridization solution will be unlabeled carrier nucleic acids from about 0.1 to 5 mg/mL, fragmented nucleic DNA, e.g., calf thymus or salmon sperm DNA, or yeast RNA, and optionally from about 0.5 to 2% wt/vol. glycine. Other additives may also be included, such as volume exclusion agents which include a variety of polar water-soluble or swellable agents, such as polyethylene glycol, anionic polymers such as polyacrylate or polymethylacrylate, and anionic saccharidic polymers, such as dextran sulfate.

Nucleic acid hybridization is adaptable to a variety of assay formats. One of the most suitable is the sandwich assay format. The sandwich assay is particularly adaptable to hybridization under non-denaturing conditions. A primary component of a sandwich-type assay is a solid support. The solid support has adsorbed to it or covalently coupled to it immobilized nucleic acid probe that is unlabeled and complementary to one portion of the rRNA sequence. Preferred are those probes that hybridize to regions of the rRNA that have minimal secondary and tertiary interactions. The advantage of such probes is that the hybridization can be carried out without the additional step of heat denaturing the sample nucleic acid. For example, the hybridization can be carried out at room temperature. Probes particularly useful in the present invention are those listed in Table 1, (SEQ ID NOs:35–60).

The sandwich assay may be encompassed in an assay kit. This kit would include a first component for the collection of samples from soil such as vials for containment, and buffers for the disbursement and lysis of the sample. A second component would include media in either dry or liquid form for the hybridization of target and probe polynucleotides, as well as for the removal of undesirable and nonduplexed forms by washing. A third component includes a solid support (dipstick) upon which is fixed or to which is conjugated unlabeled nucleic acid probe(s) that is(are) complementary to a part of the precursor rRNA of the species of bacteria being tested. In the case of multiple target analysis more than one capture probe, each specific for its own rRNA, will be applied to different discrete regions of the dipstick. A fourth component would contain labeled probe that is complementary to a second and different region of the same rRNA strand to which the immobilized, unlabeled nucleic acid probe of the third component is hybridized.

In another embodiment, the instant 16S rDNA sequence may be used as a 3' blocked detection probe in either a homogeneous or heterogeneous assay format. For example a probe generated from the instant sequences may be 3' blocked or non-participatory and will not be extended by, or participate in, a nucleic acid amplification reaction. Additionally, the probe incorporates a label that can serve as a reactive ligand that acts as a point of attachment for the immobilization of the probe/analyte hybrid or as a reporter to produce detectable signal. Accordingly, genomic or cDNA isolated from the test organism is amplified by standard primerdirected amplification protocols in the presence of an excess of the 16S rDNA 3' blocked detection probe to produce amplification products. Because the probe is 3' blocked, it does not-participate or interfere with the amplification of the target. After the final amplification cycle, the detection probe anneals to the relevant portion of the amplified DNA and the annealed complex is then captured on a support through the reactive ligand.

The probe may be several hundred bases in length where 25–65 base is preferred. The instant probe is versatile and may be designed in several alternate forms. The 3' end of the probe is blocked from participating in a primer extension reaction by the attachment of a replication inhibiting moiety. Typical replication inhibitors moieties will include but are not limited to, dideoxynuleotides, 3-deoxynucleotide, a sequence of mismatched nucleosides or nucleotides, 3' phosphate groups and chemical agents. Within the context of the present invention cordycepin (3' deoxyadenosine) is preferred.

The replication inhibitor is covalently attached to the 3' hydroxy group of the 3' terminal nucleotide of the non-participatory probe during chemical synthesis, using standard cyanoethyl phosphoramidite chemistry. This process uses solid phase synthesis chemistry in which the 3' end is covalently attached to an insoluble support (controlled pore glass -CPG) while the newly synthesized chain grows on the 5' terminus. Within the context of the present invention, 3-deoxyribonucleotides are the preferred replication inhibitors. Cordycepin, 3-deoxyadenosine, is most preferred. Since the cordycepin will be attached to the 3' terminal end of the probe, the synthesis is initiated from a cordycepin covalently attached to CPG, 5-dimethoxytrityl-N-benzoyl-3-deoxyadenosine (cordycepin), 2-succinoyl-long chain alkylamino-CPG (Glen Research, Sterling, Va.). The dimethoxytrityl group is removed and the initiation of the chain synthesis starts at the deprotected 5' hydroxyl group of the solid phase cordycepin. After the synthesis is complete, the oligonucleotide probe is cleaved off the solid support leaving a free 2' hydroxyl group on the 3'-terminally attached cordycepin. Other reagents can also be attached to the 3' ternninus during the synthesis of the non-participatory probe to serve as replication inhibitors. These include, but are not limited to, other 3-deoxyribonucleotides, biotin, dinitrophenol, fluorescein, and digoxigenin, which are also derivatized on CPG supports (Glen Research, Sterling, Va.; Clonetech Laboratories, Palo Alto, Calif.).

It is understood that the probe may be RNA or DNA or a synthetic nucleic acid, however, it will contain some sequence sufficiently complementary to the nucleic acid from the *Dehalococcoides enthenogenes*-like organisms to be detected that will permit hybridization between the detection probe and the subject DNA.

PCR Assay Methods

In an alternate embodiment the present sequences may be used as primers or to generate primers that may be used in primer directed nucleic acid amplification to detect the presence of dechlorinating bacteria. A variety of primer directed nucleic acid amplification methods are known in the art including thermal cycling methods such as polymerase chain reaction (PCR) and ligase chain reaction (LCR) as well as isothermal methods and strand displacement amplification (SDA). The preferred method is PCR. Typically, in PCR-type amplification techniques, the primers have different sequences and are not complementary to each other. Depending on the desired test conditions, the sequences of the primers should be designed to provide for both efficient and faithful replication of the target nucleic acid. Methods of PCR primer design are common and well known in the art. (Thein and Wallace, "The use of oligonucleotide as specific hybridization probes in the Diagnosis of Genetic Disorders", in *Human Genetic Diseases: A Practical Approach*, K. E. Davis Ed., (1986) pp. 33–50 IRL Press, Herndon, Va.); Rychlik, W. (1993) In White, B. A. (ed.), *Methods in Molecular Biology*, Vol. 15, pages 31–39, PCR Protocols: Current Methods and Applications. Humania Press, Inc., Totowa, N.J.)

If a nucleic acid target is to be exponentially amplified, then two primers are used each having regions complementary to only one of the stands in the target. After heat denaturation, the single-stranded target fragments bind to the respective primers which are present in excess. Both primers contain asymmetric restriction enzyme recognition sequences located 5' to the target binding sequences. Each primer-target complex cycles through nicking and polymerization/displacement steps in the presence of a restriction enzyme, a DNA polymerase and the three dNTP's and one dNTP[aS] as discussed above. An in depth discussion of SDA methodology is given by Walker et al., *Proc. Natl. Acad. Sci. U.S.A.*, 89, 392, (1992).

Alternatively, asymmetric amplification can be used to generate the strand complementary to the detection probe. Asymmetric PCR conditions for producing single-stranded DNA would include similar conditions for PCR as described however, the primer concentrations are changed with 50 pmol of the excess primer and 1 pmol of the limiting primer.

It is contemplated that this procedure would increase the sensitivity of the method. This improvement in sensitivity would occur by increasing the number of available single strands for binding with the detection probe.

Within the context of the present invention primers will be designed to conserved regions of the 16S rDNA profile which are associated with dechlorination. The most significant of those regions are the sequences set forth in SEQ ID NO: 1, SEQ ID NO:8, SEQ ID NO:30, and SEQ ID NO:34.

Following amplification and prior to sequencing, the amplified nucleotide sequence may be ligated to a suitable vector followed by transformation of a suitable host organism with said vector. One thereby ensures a more readily available supply of the amplified sequence. Alternatively, following amplification, theamplified sequence or a portion thereof may be chemically synthesized for use as a nucleotide probe. In either situation the DNA sequence of the variable region is established using methods such as the dideoxy method (Sanger, F. et al. *Proc. Natl. Acad. Sci* (1977) 74, 5463–5467). The sequence obtained is used to guide the choice of the probe for the organism and the most appropriate sequence(s) is/are selected.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

GENERAL METHODS

Standard recombinant DNA and molecular techniques used in the Examples are well known in the art. Techniques suitable for use in the following examples may be found in Sambrook, J., Fritsch, E. F. and Maniatis, T., *Molecular Cloning: A Laboratorg Manual*, Second Edition, Cold Spring Harbor Laboratory Press, Cold Spring Harbor, N.Y. (1989) (hereinafter "Maniatis").

Materials and methods suitable for the maintenance and growth of bacterial cultures are well known in the art. Techniques suitable for use in the following examples may be found as set out in *Manual of Methods for General Bacteriology*(Phillipp Gerhardt, R. G. E. Murray, Ralph N. Costilow, Eugene W. Nester, Willis A. Wood, Noel R. Krieg and G. Briggs Phillips, eds), American Society for Microbiology, Washington, D.C. (1994)) or by Thomas D. Brock in *Biotechnology: A Textbook of Industrial Microbiology*, Second Edition, Sinauer Associates, Inc., Sunderland, Mass. (1989). All reagents, restriction enzymes and materials used for the growth and maintenance of bacterial cells were obtained from Aldrich Chemicals (Milwaukee, Wis.), DIFCO Laboratories (Detroit, Mich.), GIBCO/BRL (Gaithersburg, Md.), or Sigma Chemical Company (St. Louis, Mo.) unless otherwise specified.

Manipulations of genetic sequences were accomplished using the suite of programs available from the Genetics Computer Group Inc. (Wisconsin Package Version 9.0, Genetics Computer Group (GCG), Madison, Wis.), DNASTAR (DNASTAR, Inc. 1228 S. Park St. Madison, Wis. 53715 U.S.A.), or the "on-line" Probe Match Program from the Ribosomal Database Project II (Michigan State University, East Lansing, Mich.). Where any sequence analysis software was used in the following examples, default values were used unless otherwise specified.

The meaning of abbreviations is as follows: "h" means hour(s), "min" means minute(s), "sec" means second(s), "d" means day(s), "mL" means milliliters, "L" means liters.

Example 1

Isolation and Characterization of Dechlorinating Soil Organisms

Aquifer core samples were obtained by split spoon sampling at depths ranging from 10 to 80 ft, depending on the depth of the particular aquifer to be tested. The cores were taken in sterile stainless steel cylinders or placed in sterile glass vials. The core samples were immediately shipped to the laboratory at ambient temperatures and under anaerobic conditions. Upon arrival the samples were stored in an anaerobic glove bag (chamber) (Coy Laboratory Products Inc., Ann Arbor, Mich.), whose atmosphere was 10% $H_2$, 5% $CO_2$ and 85% $N_2$.

The laboratory microcosms were prepared in 250 mL Wheaton bottles (Wheaton Co., Millville, N.J.) within the anaerobic chamber. Duplicate microcosms were prepared for the following conditions: Killed Control (live soil autoclaved for 1 hr on 2 consecutive days), Live soil, and Live soil+0.05% yeast extract Each microcosm contains 20% soil and 80% BTZ-3 media ($NH_4Cl$, 4.3 g/L; $KH_2PO_4$, 50 g/L; $MgCl-6H_2O$, 20 g/L; $CaCl_2-2H_2O$, 1 g/L; HEPES, 50 mM/L; mineral solution, 10 mL/L; resazurin 0.2%, 5 mL/L). The microcosm were filled to top such there was little or no headspace, and then stoppered with Teflon™ lined disks and crimp-sealed with aluminum seals (Wheaton Co., Miliville, N.J.). The resazurin addition permitted the visualization of low potential anaerobic conditions by a color change from pink to colorless. Each microcosm was spiked with 5 ppm from a PCE or TCE solution saturated in water. The microcosms were incubated on their sides in the anaerobic chamber, in the dark, at ambient room temperature (22° C.) for up to 180 days.

Samples were analyzed the next day as time zero ($t_0$) and then twice a week for the dechlorination of PCE or TCE and the formation of cisDCE, vinyl chloride or methane. All samples were taken in the anaerobic chamber by using a syringe mounted with a 23 gauge needle was use to puncture the Teflon™ septa to obtain a 5 mL liquid sample that was injected into a 10 mL headspace vial. Samples were tested using HP Headspace sampler 7694, HP5890 series II GC (FID detector, HP 5 capillary column #19091J-215), HP3365 Chemstation version A.03.34.

FIG. 3 plots the concentration (parts per million; ppm) of chloroethenes in the microcosm medium as a function of time (days) and illustrates the dechlorination of chloroethenes. Dechlorination of PCE to TCE could be detected by GC/FID. Within two days with the formation of cisDCE from the dechlorination of TCE was detected. These results are found in the microcosms that has been amended with 0.05% yeast extract plus minimal salts media (BTZ-3 media). These results can also be seen in the microcosms that are amended with the minimal salts media alone. The difference is the dechlorination is slightly delayed. It takes four days before cisDCE is detected. Degradation of cisDCE would occur over the next two weeks. Vinyl chloride and ethene could only be detected at trace levels. The "Killed" control, did not show degradation of PCE or TCE during the duration of the experiment. Cell growth was shown by increase in the turbidity of the microcosm medium and by microscopic analysis.

Example 2

Generation of PCR Primers and Probes for the Amplification and Detection of the *Dehalococcoides Ethenozenes* 16S rRNA Profiled The detection and sequencing of the *Dehalococcoides enthenogenes*-like organisms used the set of PCR primers are shown in Table 1 (SEQ ID NO:9–29). The PCR primers were designed using signature sequence regions. To determine the location of these signature sequence, the *Dehalococcoides enthenogenes* sequence (GenBank No. AF004928)[SEQ ID NO:7] was aligned using MEGALIGN (DNAstar, Madison, Wis.) or Pileup (Genetics Computer Group, Madison, Wis.) with 16S rRNA sequences from 100 organisms that represent most major domains, families and genera in the major kingdoms of Bacteria and Archaea. The conserved, variable, and highly variable regions could be delineated by boxing off the consensus sequences. Primer candidate sequences were manually picked from the variable and highly variable regions and then their uniqueness was determined by determining their potential as probes to a ribosomal sequence database sequences using the "on-line" Probe Match Program from the Ribosomal Database Project II RDPII, Michigan State University, East Lansing, Mich.).

This analysis returned an overview of the matches between a probe and its potential target sequence, as a listing and as a phylogenetic overview. The program results showed the sequences that match the query sequence (if there are such sequences) and also showed sequences that had mismatches, deletions and insertions, citing the number and positions of the aberrations.

The sequences which were unique and passed this test as signature sequences were then designed as either a forward or reverse primer, usually dependent on their position in the sequence. The most unique sequence of the signature sequence (specificity) was designed into the 3' end in either type of primer. The selected primers are shown in Table 1.

The primers were synthesized using standard β-cyanoethyl phosphoramidite coupling chemistry on controlled pore glass (CPG) supports on automated DNA oligonucleotide synthesizer (Applied Biosystems Model 392, Perkin-Elmer, Foster City, Calif.)

The primers were tested after they were synthesized using PCR on samples taken from microcosms known to have *Dehalococcoides enthenogenes*-like organisms. The PCR products were sized on agarose electrophoresis and then cloned and sequenced to verify that the amplified sequences were *Dehalococcoides enthenogenes*-like 16S rRNA sequences.

TABLE 1

Primers for *Dehalococcoides ethenogenes*

| | | |
|---|---|---|
| FP DHE 32 | 5'AAG TCGAACGGTCTTAAGCA3' | (SEQ ID NO: 9) |
| RP DHE422 | 5' CGTCATTATTCTTCCCTGTG 3' | (SEQ ID NO: 10) |
| FP DHE 958 | 5'GGGAAACGACCTGTTAAGTCA 3' | (SEQ ID NO: 11) |
| RP DHE 1212 | 5'GGATTAGCTCCAGTTCACACTG 3' | (SEQ ID NO: 12) |
| RP DHE 1076 | 5'AAATTTAACTAGCAACAAGG 3' | (SEQ ID NO: 13) |
| FP DHE 775 | 5'GGAGTATCGACCCTCTCTG 3' | (SEQ ID NO: 14) |
| FP DHE 774 | 5'GGGAGTATCGACCCTCTC 3' | (SEQ ID NO: 15) |
| FP DHE 946 | 5'AGTGAACCGAAAGGGAAA 3' | (SEQ ID NO: 16) |
| FP DHE 385 | 5'GGGTTGTAAACCTCTTTTCAC 3' | (SEQ ID NO: 17) |
| RP DHE 806 | 5'GTTAGCTTCGGCACAGAGAG 3' | (SEQ ID NO: 18) |
| RP DHE 692 | 5'TCAGTGACAACCTAGAAAAC 3' | (SEQ ID NO: 19) |
| FP DHE1 | 5'GATGAACGCTAGCGGCG 3' | (SEQ ID NO: 20) |
| FP DHE 30 | 5'GTGCCTTATGCATGCAAG 3' | (SEQ ID NO: 21) |
| FP DHE 1187 | 5' AATAGGTTGCAACAGTGTGAA 3' | (SEQ ID NO: 22) |
| FP DHE 1175 | 5' AATGGACAGAACAATAGGTTGC 3' | (SEQ ID NO: 23) |
| RP DHE 1381 | 5' GGCACATCGACTTCAAGTGTT 3' | (SEQ ID NO: 24) |
| FP DHE 385A | 5' GGGTTGTAAACCTCTTTTCA 3' | (SEQ ID NO: 25) |
| FP DHE 558 | 5' TAACCGGGACG(AT)GTCATTCA 3' | (SEQ ID NO: 26) |
| FP DHE 593 | 5' GAGTACAGCAGGAGAAAAC 3' | (SEQ ID NO: 27) |
| RP DHE 1387 | 5' CCTCCTTGCGGTTGGCACATC 3' | (SEQ ID NO: 28) |
| RP DHE 1090 | 5' GGCAGTCTCGCTAGAAAAT 3' | (SEQ ID NO: 29) |
| dAB pDHE A (141–173) | 5' TGTGATGGGCTGACATAAGTCGGTTCATTAAAGCCGCAAGGTG 3' | (SEQ ID NO: 35) |
| | 5' CACCTTGCGGCTTTAATGAACCGACTTATGTCAGCCCATCACA 3' | (SEQ ID NO: 36) |
| pDHE B (141–173) | 5' TGTGGTGGGCCGACATAAGTTGGTTCACTAAAGCCGTAAGGTG 3' | (SEQ ID NO: 37) |
| | 5' CACCTTACGGCTTTAGTGAACCAACTTATGTCGGCCCACCACA 3' | (SEQ ID NO: 38) |
| pDHE C (141–173) | 5' TGTGGTGGGCCGACATATGTTGGTTCACTAAAGCCGTAAGGCG 3' | (SEQ ID NO: 39) |
| | 5' CGCCTTACGGCTTTAGTGAACCAACATATGTCGGCCCACCACA 3' | (SEQ ID NO: 40) |
| pDHE (1068–1105) | 5' AGTTAAATTTTCTAGCGAGACTGCCCCGCGAAACGG 3' | (SEQ ID NO: 41) |
| | 5' CCGTTTCGCGGGGCAGTCTCGCTAGAAAATTTAACT 3' | (SEQ ID NO: 42) |
| pDHE (1068–1096) | 5'AGTTAAATTTTCTAGCGAGACTGCCCCGC 3' | (SEQ ID NO: 43) |
| | 5' GCGGGGCAGTCTCGCTAGAAAATTTAACT 3' | (SEQ ID NO: 44) |
| pDEH (1057–1086) | 5' CCTTGTTGCTAGTTAAATTTTCTAGCGAGA 3' | (SEQ ID NO: 45) |
| | 5' TCTCGCTAGAAAATTTAACTAGCAACAAGG 3' | (SEQ ID NO: 46) |
| pDHE (932–963) | 5' GACATGCATGAAGTAGTGAACCGAAAGGGAAA 3' | (SEQ ID NO: 47) |
| | 5' TTTCCCTTTCGGTTCACTACTTCATGCATGTC 3' | (SEQ ID NO: 48) |
| pDHE (565–594) | 5'GGACGTGTCATTCAATACTGTTGGACTAGA3' | (SEQ ID NO: 49) |
| | 5'TCTAGTCCAACAGTATTGAATGACACGTCC3' | (SEQ ID NO: 50) |
| pDHE (582–613) | 5' TGTTGGACTAGAGTACAGCAGGAGAAAACGGA 3' | (SEQ ID NO: 51) |
| | 5' TCCGTTTTCTCCTGCTGTACTCTAGTCCAACA 3' | (SEQ ID NO: 52) |

TABLE 1-continued

Primers for *Dehalococcoides ethenogenes*

| | | |
|---|---|---|
| pDHE (555–582) | 5' GGCTTAACCGGGACGTGTCATTCAATACT 3' | (SEQ ID NO: 53) |
| | 5' AGTATTGAATGACACGTCCCGGTTAAGCC 3' | (SEQ ID NO: 54) |
| pDHE (547–582) | 5' AATTTCCCGGCTTAACCGGGACGTGTCATTCAATACT 3' | (SEQ ID NO: 55) |
| | 5' AGTATTGAATGACACGTCCCGGTTAAGCCGGGAAATT 3' | (SEQ ID NO: 56) |
| pDHE (969–999) | 5' TGTTAAGTCAGGAGTTTGCACAGGTGCTGCA 3' | (SEQ ID NO: 57) |
| | 5' TGCAGCACCTGTGCAAACTCCTGACTTAACA 3' | (SEQ ID NO: 58) |
| pDHE (80–110) | 5' CGCGTAAGTAACCTACCTCTAAGTGGGGGAT 3' | (SEQ ID NO: 59) |
| | 5'ATCCCCCACTTAGAGGTAGGTTACTTACGCG 3' | (SEQ ID NO: 60) |

Example 3

Using the *Dehalococcoides Ethenogenes*-Like Specific Primers to Detect These Organisms in Microcosms Nucleic acids were extracted from the microcosm cultures by a bead mill homogenization procedure, FastDNA Spin Kit for Soil (Bio 101, Vista, Calif.), that was designed to isolate genomic DNA from all cell types. Approximately 10 mL of the microcosm culture was pelleted and resuspended in 500 µl of the culture media. The resuspended pellet was added to a 2.2 mL conical screw-cap tube containing 1.5 g of three differently sized glass and zirconia/silica beads (106 microns, 710–1180 microns). To the sample tubes, 978 ul of sodium phosphate buffer and 122 ul of MT buffer was added. The tubes were homogenized for 30 seconds at speed 5.5 on a Fast Prep bead mill homogenizer. A clear supernatant was obtained by centrifuging the samples at 14,000×g for 30 seconds. The supernatant was transferred to a clean microcentrifuge tube and 250 ul of PPS reagent was added and mixed. The resulting precipitate was pelleted through centrifugation at 14,000×g for 5 minutes. The supernatant was transferred to a new microcentrifuge tube and 1 mL of binding matrix was added. The samples were placed on a rotator for 2 minutes and then sat on the benchtop for 3 minutes to allow the settling of the silica matrix. Between 500–700 ul of the supernatant was removed and discarded. The remaining supernatant was used to resuspend the silica matrix and transferred to a spin filter. The spin filter was centrifuged for 1 minute at 14,000×g and the flow-through decanted. The silica matrix was washed with 500 ul of SEWS-M buffer and centrifuged for 1 minute at 16,000×g. The flow through was discarded and any residual buffer in the matrix was removed by a 2 minute centrifugation at 14,000×g. The spin filter was placed in a catch tube and air dried for 5 minutes in a biological hood. The genomic DNA was eluted by adding 60 ul of sterile, deionized water, mixing the matrix and the water together with a pipet tip, and centrifuging for 1 minute at 14,000×g.

The 16S rRNA gene for *Dehalococcoides enthenogenes* was detected by PCR amplification and gel electrophoresis. The 16S sequences were amplified using *Dehalococcoides enthenogenes* specific 16S rDNA primers shown in Table 1. All PCR amplifications were performed using the GeneAmp PCR kit with Taq DNA polymerase (PE Applied Biosystems, Branchburg, N.J.) in a Perkin Elmer 9600 thermal cycler Amplification reactions contained 10 mM Tris-HCl (pH 8.3), 50 mM KCl, 1.5 mM $MgCl_2$, 10 µM each deoxynucleoside triphosphate, 20 pmol each primer, 2.5 U of Taq polymerase, and 1 µL of the genomic extraction diluted 1:10 in a final reaction volume of 50 µL. The PCR conditions were as follows: 2 minutes of denaturation at 95° C., followed by 30 cycles of 30 seconds at 94° C., 30 seconds at 55° C., 30 seconds at 72° C. 8 µL of the PCR product was visualized on a 2% agarose gel (SeaKem GTG, FMC BioProducts, Rockland, Me.) stained with ethidium bromide.

A direct detection protocol used 1 µL of the microcosm culture was directly added to the PCR as described previously.

After the *Dehalococcoides enthenogenes*-like sequences were detected in the microcosm developed from contaminated soil, FP DHE 1 (SEQ ID NO:20), RP DHE 1330 (SEQ ID NO:12) were used to amplify a 1212 bp fragment, which was cloned (using the PCR dA/T-Cloning System, Invitrogen, Inc., Calif.) and sequenced (using Model 377 DNA Sequencer kit and system, Applied Biosystems, Perkin-Elmer, Foster City, Calif.). The sequence was assembled using the Seqman II program (DNAstar, Inc., Madison, Wis.). The 16S rDNA sequence contig formed was compared to 16S rDNA sequences obtained from microcosms developed from contaminated soils from other sites and the comparison is shown in FIG. 4.

Figure 4:
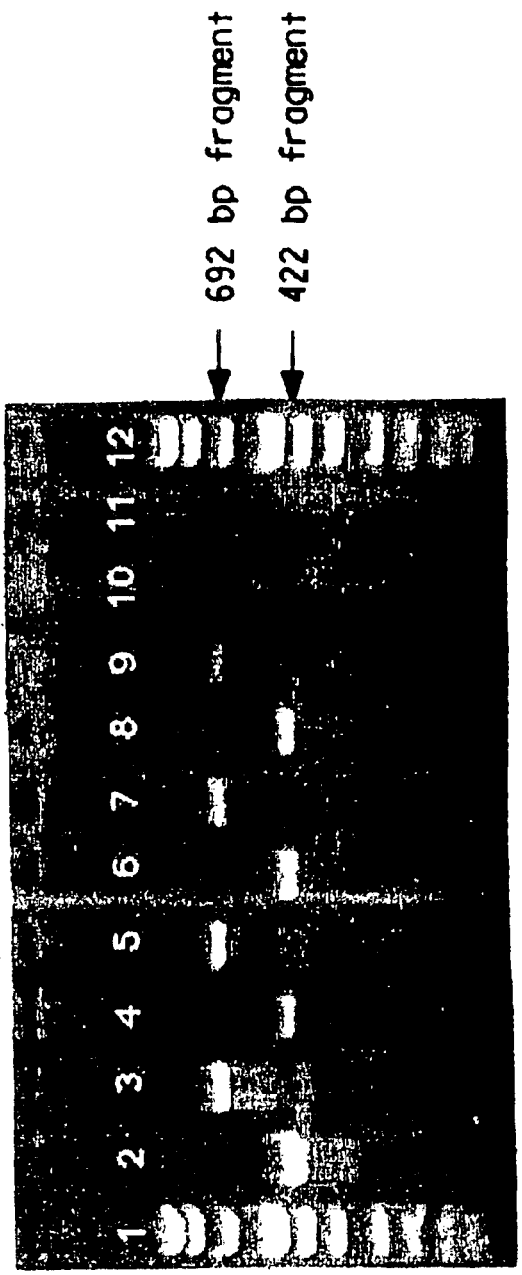
FIG. 4 is an image of an electrophoresis gel used to detect PCR products in a test of soils contaminated with chloroethenes using two sets of the primers described herein.

FIG. 4 shows a gel of amplification products generated from PCR amplification of various *Dehalococcoides enthenogenes* isolated from a number of industrial sites contaminated with either PCE or TCE. All amplifications were carried out using primers SEQ ID NOs:17 paired with 19, and SEQ ID NOs:18 paired with 20. Lanes 1 and 12 carry the molecular weight markers. Lanes 2 and 3 are the PCR products generated from organisms isolated from soil containing PCE. Lanes 4, 5, 6, 7, 8 and 9 are the PCR products from organisms isolated from soil containing TCE. Lanes 10 and 11 contain negative PCR controls. As can be seen by the data all samples were detectable by the primers used.

The contiguous sequences from each site was unique, having 96 to 99% similarity to each other. The differences in the sequence are annotated in Table 2. A major difference exists in the consensus sequence that were obtained from all strains (CS) detected at contaminated sites and the reference sequence represented by the published sequence from strain DHE-195 strain (Table 2). At DHE (CS) positions 1088–1096 (*E. coli* coordinates E1146–E1156) there exists a nine base deletion. The sequence in CS strains reads ATTTTCTAGCGAGACTG (SEQ ID NO:31); in the DHE-195 strain it reads ATTTTCTAGCGAG<u>ACTAGCGAG</u>ACTG (SEQ ID NO:32) (the double underlined sequence is the sequence deleted in the CS strain sequences. Differences in sequence were found at six other base positions as shown below in Table 2.

TABLE 2

| E. coli | DHE No. | DHE-195 | | Sig. Grp | DHE-P1 | | DHE-stf | | DHE D11 | | DHE Pin | |
|---|---|---|---|---|---|---|---|---|---|---|---|---|
| 28 | 1 | | 1 | | | 1 | | 1 | | 1 | | 1 |
| 107 | 66 | A | 66 | 6A | A | 66 | A | 66 | A | 66 | G | 66 |
| 184 | 144 | A | 144 | 2A | A | 144 | G | 144 | G | 144 | G | 144 |
| 190 | 150 | T | 150 | 2B | T | 150 | C | 150 | C | 150 | C | 150 |
| 197 | 157 | A | 157 | 6B | A | 157 | A | 157 | A | 157 | T | 157 |
| 200 | 160 | C | 160 | 2C | C | 160 | T | 160 | T | 160 | T | 160 |
| 207 | 167 | T | 167 | 2D | T | 167 | C | 167 | C | 167 | C | 167 |
| 216 | 176 | C | 176 | 2E | C | 176 | T | 176 | T | 176 | T | 176 |
| 221 | 181 | T | 181 | 6C | T | 181 | T | 181 | T | 181 | C | 181 |
| 264 | 226 | T | 226 | 3A | T | 226 | C | 226 | C | 226 | T | 226 |
| 267 | *229 | T | 229 | 1A | C | 229 | C | 229 | C | 229 | C | 229 |
| 291+ | 254 | d | 253+ | 5A | d | 253+ | T | 254 | d | 253+ | d | 253+ |
| 333 | *296 | G | 295 | 1B | C | 295 | C | 296 | C | 295 | C | 295 |
| 420 | 383 | T | 382 | 3B | T | 382 | C | 383 | C | 382 | T | 382 |
| 444 | 407 | C | 406 | 6D | C | 406 | C | 407 | C | 406 | T | 406 |
| 542 | *481 | G | 480 | 1C | d | 479+ | d | 480+ | d | 479+ | d | 479+ |
| 631 | 571 | T | 570 | 6E | T | 569 | T | 570 | T | 569 | A | 569 |
| 829 | 769 | G | 768 | 5B | G | 767 | A | 768 | G | 767 | G | 767 |
| 933 | 874 | G | 873 | 4A | T | 872 | G | 873 | G | 872 | G | 872 |
| 934 | 875 | C | 874 | 4B | T | 873 | C | 874 | C | 873 | C | 873 |
| 980 | *921 | d | 919+ | 1D | C | 919 | C | 920 | C | 919 | C | 919 |
| 1003 | 944 | A | 942 | 6F | A | 942 | A | 943 | A | 942 | T | 942 |
| 1012 | 955 | C | 953 | 6G | C | 953 | C | 954 | C | 953 | T | 953 |
| 1020 | 963 | A | 961 | 6H | A | 961 | A | 962 | A | 961 | G | 961 |
| 1039 | 984 | G | 982 | 6I | G | 982 | G | 983 | G | 982 | A | 982 |
| 1040 | 985 | T | 983 | 6J | T | 983 | T | 984 | T | 983 | C | 983 |
| 1087 | *1033 | G | 1031 | 1E | T | 1031 | T | 1032 | T | 1031 | T | 1031 |
| 1114 | *1060 | d | 1057+ | 1F | C | 1058 | C | 1059 | C | 1058 | C | 1058 |
| 1144–56 | *1088–96 | 1086–94 ACTAGCG AG | | 1G | d | 1085+ | d | 1086+ | d | 1085+ | d | 1085+ |
| 1284 | 1225 | C | 1220 | 3C | C | 1213 | T | 1214 | T | 1213 | C | 1213 |
| 1364 | 1304 | A | 1300 | 6K | A | 1292 | A | 1293 | A | 1292 | T | 1292 |
| 1427 | 1357 | N | 1353 | 1H | A | 1345 | A | 1346 | A | 1346 | A | 1346 |

"DHE No." represents Consensus sequence number;

Sequence number with (+) represents last base coordinate before a base a deletion;

Bold bases are indicative of base sequences different from DHE 195;

Bold bases and blockscells (base and coordinate) imply sequence of all 16S sequences isolates that are different from DHE strain 195 "Sig. Grp" indicates which set of Signature Sequences Set a bases belongs to.

"1(Letter)" Signature group: sequences in entire DHE group 16S rDNA sequence are different from the Cornell strain 195 at designated positions "2(Letter)" Signature group: sequences are unique to DHE (stf), DHE (D11) and DHE (Pnl/Dab) at designated positions "3(Letter)" Signature group: sequences are unique to DHE (stf) and DHE (D11) at designated positions "4(Letter)" Signature group: sequences are unique to DHE (P1) at designated positions "5(Letter)" Signature group: sequences are unique to DHE (stf) at designated positions "6(Letter)" Signature group: sequences are unique to DHE (Pnl/Dab) at designated positions All sequences generated using species-specific primers for *Dehalococcoides ethenogenes* were found to have identity with *Dehalococcoides enthenogenes* Strain 195. Sequence identities ranged from 98.5 to 99.6% and were defined as "*Dehalococcoides ethenes*-like" sequences since the 16S rDNA sequences did not completely match the 16S rDNA sequence of Strain 195. The PCR products produced by from either FP DHE 1 (SEQ ID NO:20)and RP DHE 1212 (SEQ ID NO:12)or FP DHE 1 (SEQ ID NO:1) and RP DHE 1387 (SEQ ID NO:28) were the longer amplified products (1212 or 1387 bp in length, respectively). The differences between each sequence and the sequence of *D. ethenogenes*' Strain 195 (GenBank AF004928), are shown in Table 2. The *Dehalococcoides enthenogenes*-like 16S rDNA sequences from any one contaminated site were different than those *Dehalococcoides enthenogenes*-like 16S rDNA sequences obtained from microcosm samples from the other sites. PCR products, which were taken at different time points from the same microcosms, also yielded the same 16S rDNA sequence. It appears that the *D. ethenogenes*-like 16S rDNA sequences are unique to the specific site of origin. All four 16S rDNA sequences were found to be different from Strain 195 sequence at seven sequence positions (designated by 1A to 1G signature positions, Table 2 in the Sig. column).

There are three single base substitutions (1A, 1B and 1E), one single-base deletion (1C) and two single-base insertions (1D and 1F). All sequences also shared a nine base deletion located at Strain 195 base number 1085 (Table 2).

The DHE-P1 16S rDNA sequences were the closest to the 16S rDNA sequence of Strain 195 (99.6% identity). It has nine base changes (signature groups 1 and 4, Table 2): 6 base substitutions, one deletion (excluding the 9 base deletion error) and 2 insertions). The DHE-Pin 16S rDNA sequence was the most distant from Strain 195 with 24 base changes (98.5% identity, signature groups 1, 2, 6 in Table 2). The DHE-V/Sfd (99.1% identity) and the DHE-D11 (99.2% identity) 16S rDNA sequences were found to share 15 differences (signature group 1, 2 and 3 in Table 2) from the sequence of Strain 195. In addition, the DHE-STF sequence differed from the DHE-D11 sequence with a single base insertion (5A) and a single base substitution (5B).

Signature sequences 2 and 6 have unique base substitutions that distinguish the 16S rDNA sequences that are found in the DHE STF culture, the DHE-D11 and the DHE-Pin from the Strain 195 16S rDNA sequence. The STF and Pin 16S rDNA sequences have base substitutions at base positions: 144 (A→G), 150 (T→C), 160(C→T), 167 (T→C) and 176 (C→T). Further, the Pin 16S rDNA sequence has base substitutions in region 2 at base positions: 157 (A→T) and 181(T→C) that makes its sequence different from those of Strain 195 and STF. These base substitutions in region 2 are conserved (Table 2, Signature groups 2A to 2E and 6A to 6B) and are being used in the signature sequence definitions of these 16S rDNA sequences. The DHE-P1 16S rDNA sequence in signature sequence 2 is identical to Strain 195. The DHE-D11 16S rDNA sequence in signature sequence 2 is identical to the sequence from DHE-STF.

In signature sequence 6, the DHE-Pin 16S sequence is different from the sequences of all the other *Dehalococcoides enthenogenes*-like 16S rDNA sequences, including that of Strain 195. Its sequence has base substitutions at base positions: 942 (A→T), 952 (C→T), 961 (A→G), 982 (G→A) and 983 (T→C) (Table 2, 6 F to 6 K). In conjunction with signature sequence 2, signature sequence 6 is used to define of the DHE-Pin 16S rDNA sequence.

Example 4

Using the *Dehalococcoides Ethenogenes*-Like Specific Primes and Probe to Detect Dehalococcoides in a Test-Kit This Example demonstrates the detection of *Dehalococcoides enthenogenes*-like organisms in a test kit using the 16S rRNA gene sequences for test primers and probe reagents.

Materials

The following reagents and materials for assembly of the test kit were purchased commercially. Nitrocellulose membrane (5.0 μm porosity) was purchased from Schleicher & Schuell (Keene, N.H. 03431) as 15 cm×15 cm sheets. Alkaline phosphatase NBT/BCIP substrate (0.12 mM) was purchased from Moss, Inc., (Pasadena, Md. 21123-0189), and Streptavidin from ZYMED Lab., Inc. (Calif.). Anti-Digoxigenin Alkaline Phosphatase Conjugate Fab fragments (1093-274) and Digoxigenin-11-dUTP (1558706) were purchased from the Boehringer Mannheim Corp. Adsorptive pads (0.33 mm thickness) were purchased from VWR Scientific (28303) and pad #50970 from Schleicher & Schuell (Keene, N.H. 03431).

Preparation of Test Kit Reagents

Lateral Flow buffer for the test kit was prepared containing 10 mM Tris Base (pH 8.0), (J. T. Baker Inc., Phillipsburg, N.J.), 150 mM NaCl, 1 mM $MgCl_2$, 0.1 mM $ZnCl_2$, 0.5% bovine serum albumen, 0.1% Triton X100 in purified water.

Wash Buffer for the test kit was prepared containing 100 mM Tris Base (pH 9.5), (J. T. Baker Inc., Phillipsburg, N.J.) 100 mM NaCl, 50 mM $MgCl_2$, in purified water.

Detection probes and primers for the test kit were based on the Dehalococcoide sequences in Table 1. The primers and probes were synthesized using standard cyanoethyl phosphoramidite chemistry on a Perkin Elmer Biosystems model 392. The probe labels (N) were substituted for nucleotides during synthesis using commercially labeled phosphoramidite reagents that possess 2 aminobutyl-1,3-propanediol backbone or 1-(1,2 diaminoethane) 3-deoxyfructonic acid. In the sequence, cordycepin 5' triphosphate (3' deoxyadenosine) is indicated by, "dA" and biotin Label-ON Phosphoramidite® (Clontech, Palo Alto, Calif.) by "B". Specifically, the following primers and probes were used in detection:

*Dehalococcoides Ethenogenes* Target-specific Primers

Forward Primer DHE 385: (SEQ ID NO:17)
Reverse Primer DHE 807(806): (SEQ ID NO:18)
Detection Probe (Biotin labeled) dD-B DHE 555 B2:
5'BGGCTTAACCGGGACGTGTCATTCAATACBdA 3'(SEQ ID NO:53)

A test strip capture reagent was prepared for the test kit assay by printing Streptavidin (0.1 μL of 5 mg/ml) either as a transverse line across a nitrocellulose membrane or as a alpha numeric letter (Schleicher & Schull, Keene, N.H., >5 μ porosity). The Streptavidin was printed near the efferent end (capture zone) of the membrane. Prior to use, the printed membrane was then stored in desiccator at room temperature for 3 days. The test strip membrane was then supported horizontally in a plastic holder. An adsorbent pad 0.33 mm in thickness (VWR Scientific, #28303) was then placed on the test strip ca. 1 cm above the capture zone to adsorb and collect test fluids.

Sample DNA Extraction and Detection

DNA for detection in the test kit was prepared as follows. The nucleic acids were extracted from dechlorinating microcosm cultures by a bead mill homogenization procedure, FastDNA Spin Kit for Soil (Bio 101, Vista, Calif.), that was designed to isolate genomic DNA from all cell types. Approximately 10 mL of the microcosm culture was pelleted and resuspended in 500 μl of the culture media. The resuspended pellet was added to a 2.2 mL conical screw-cap tube containing 1.5 g of three differently sized glass and zirconia/silica beads (106 microns, 710–1180 microns). To the sample tubes, 978 ul of sodium phosphate buffer and 122 ul of MT buffer were added. The tubes were homogenized for 30 seconds at speed 5.5 on a Fast Prep bead mill homogenizer. A clear supernatant was obtained by centrifuging the samples at 14,000×g for 30 seconds. The supernatant was taansferred to a clean microcentrifuge tube and 250 ul of PPS reagent was added and mixed. The resulting precipitate was pelleted through centrifugation at 14,000×g for 5 minutes. The supernatant was transferred to a new microcentrifuge tube and 1 mL of binding matrix was added. The samples were placed on a rotator for 2 minutes and then sat on the benchtop for 3 minutes to allow the settling of the silica matrix. Between 500–700 ul of the supernatant was removed and discarded. The remaining supernatant was used to resuspend the silica matrix and transferred to a spin filter. The spin filter was centrifuged for 1 minute at 14,000×g and the flow-through decanted. The silica matrix was washed with 500 ul of SEWS-M buffer and centrifuged for 1 minute at 16,000×g. The flow through was discarded and any residual buffer in the matrix was removed by a 2 minute centrifugation at 14,000×g. The spin filter was placed in a catch tube and air dried for 5 minutes in a biological hood. The genomic DNA was eluted by adding 60 ul of sterile, deionized water, mixing the matrix and the water together with a pipette tip, and centrifuging for 1 minute at 14,000×g.

Following extraction, the 16S rRNA gene for *Dehalococcoides enthenogenes* was amplified by PCR and the *Dehalococcoides enthenogenes* specific DNA products detected in the test kit. In this process, the PCR amplifications were performed by using the GeneAmp PCR kit with AmpliTaq® DNA polymerase (PE Applied Biosystems, Branchburg, N.J.) in a Perkin Elmer 9600 thermal cycler. Amplification reactions contained 10 mM Tris-HCl (pH 8.3), 50 mM KCl, 1.5 mM $MgCl_2$, 100 µM each deoxynucleotide triphosphate, 20 pmol each primer, 0.5 U of AmpliTaq® polymerase, 20 pmoles detection probe, 1 mnole of Dipoxigenin-11-dUTP and 1 µL of the genomic extraction diluted 1:10 in a final reaction volume of 50 µL. The PCR conditions were as follows: 2 minutes of denaturation at 95° C., followed by 30 cycles of 30 seconds at 94° C., 30 seconds at 55° C., 30 seconds at 72° C.

For detection of the Dehalococcoides 16S rRNA gene products, the PCR test reaction mixture (10 µL) was diluted with 70 µL of lateral flow buffer. The membrane holder was placed horizontally on a bench top. The diluted PCR products (70 µL) were then applied to the sample end of the test strip and allowed to wick through the membrane reagent. This is accomplished in ca. 5 min. Diluted conjugate reagent (80 µl), prepared as a 1:25 fold dilution of the anti-digoxigenin alkaline phosphatase conjugate (Boehringer Mannheim Corp. (#1093-274) in lateral flow buffer, was then added to the sample end of the membrane and allowed to wick through the membrane and equilibrate for 10 min. This was followed by addition of 80 µL of a wash buffer to the sample end of the membrane. After 10 min, 90 µL of BCIP/NBT alkaline phosphatase substrate reagent (Moss Inc., Pasadena, Md. 21123-0189, product NBTM-1000) was added at the sample end and allowed to wick through the membrane. Test results were then read after 10 min. by visually inspecting the membrane DNA capture zone. The presence of 16S RNA gene products are evident by the formation of blue color in the form of the Streptavidin capture reagent printed on the membrane (line or alpha numeric test symbol). A visual color response exceeding background color of the membrane is indicative of the presence of the Dehalococcoides organisms DNA in the test sample.

What is claimed is:

1. An isolated 16S rDNA sequence indicative of a dechlorination bacterial strain selected from the group consisting of:

(a) SEQ ID NO:8, and (b) an isolated nucleic acid molecule that is completely complementary to (a) wherein said sequence is indicative of a dechlorinating bacterial strain.

* * * * *

SEQUENCE LISTING

<160> NUMBER OF SEQ ID NOS: 60

<210> SEQ ID NO 1
<211> LENGTH: 24
<212> TYPE: DNA
<213> ORGANISM: Dehalococcoides ethenogenes

<400> SEQUENCE: 1
attttctagc gagactgccc cgcg                                           24

<210> SEQ ID NO 2
<211> LENGTH: 1377
<212> TYPE: DNA
<213> ORGANISM: Dehalococcoides ethenogenes strain PL

<400> SEQUENCE: 2
gatgaacgct agcggcgtgc cttatgcatg caagtcgaac ggtcttaagc aattaagata     60
gtggcaaacg ggtgagtaac gcgtaagtaa cctacctcta agtgggggat agcttcggga    120
aactgaaggt aataccgcat gtgatgggct gacataagtc ggttcattaa agccgcaagg    180
tgcttggtga ggggcttgcg tccgattagc tagttggtgg ggtaatggcc taccaaggct    240
tcgatcggta gctggtctga gaggatgatc agccacactg ggactgagac acggcccaga    300
ctcctacggg aggcagcagc aaggaatctt gggcaatggg cgaaagcctg acccagcaac    360
gccgcgtgag ggatgaaggc tttcgggttg taaacctctt ttcacaggga agaataatga    420
cggtacctgt ggaataagct tcggctaact acgtgccagc agccgcggta atacgtagga    480
agcaagcgtt atccggattt attgggcgta aagtgagcgt aggtggtctt tcaagttgga    540
tgtgaaattt cccggcttaa ccgggacgtg tcattcaata ctgttggact agagtacagc    600
aggagaaaac ggaattcccg gtgtagtggt aaaatgcgta gatatcggga ggaacaccag    660
aggcgaaggc ggttttctag gttgtcactg acactgaggc tcgaaagcgt ggggagcgaa    720

```
cagaattaga tactctggta gtccacgcct taaactatgg acactaggta tagggagtat    780
cgaccctctc tgtgccgaag ctaacgctyt aagtgtcccg cctggggagt acggtcgcaa    840
ggctaaaact caaaggaatt gacgggggcc cttacaagca gcggagcgtg tggtttaatt    900
cgatgctaca cgaagaacct taccaagatt tgacatgcat gaagtagtga accgaaaggg    960
aaacgacctg ttaagtcagg agtttgcaca ggtgctgcat ggctgtcgtc agctcgtgcc   1020
gtgaggtgtt tggttaagtc ctgcaacgag cgcaacccct gttgctagtt aaatttttcta   1080
gcgagactgc cccgcgaaac ggggaggaag gtggggatga cgtcaagtca gcatggcctt   1140
tatatcttgg gctacacaca cgctacaatg gacagaacaa taggttgcaa cagtgtgaac   1200
tggagctaat ccccaaagct gtcctcagtt cggattgcag gctgaaaccc gcctgcatga   1260
agttggagtt gctagtaacc gcatatcagc aaggtgcggt gaatacgttc tcgggccttg   1320
tacacaccgc ccgtcacgtc atgaaagccg gtaacacttg aagtcgatgt gccaacc      1377
```

<210> SEQ ID NO 3
<211> LENGTH: 1378
<212> TYPE: DNA
<213> ORGANISM: Dehalococcoides ethenogenes strain V/SFD

<400> SEQUENCE: 3

```
gatgaacgct agcggcgtgc cttatgcatg caagtcgaac ggtcttaagc aattaagata     60
gtggcaaacg ggtgagtaac gcgtaagtaa cctacctcta agtgggggat agcttcggga    120
aactgaaggt aataccgcat gtggtgggcc gacataagtt ggttcactaa agccgtaagg    180
tgcttggtga ggggcttgcg tccgattagc tagttggtgg ggtaacggcc taccaaggct    240
tcgatcggta gcttggtctg agaggatgat cagccacact gggactgaga cacggcccag    300
actcctacgg gaggcagcag caaggaatct tgggcaatgg gcgaaagcct gacccagcaa    360
cgccgcgtga gggatgaagg ctctcgggtt gtaaacctct tttcacaggg aagaataatg    420
acggtacctg tggaataagc ttcggctaac tacgtgccag cagccgcggt aatacgtagg    480
aagcaagcgt tatccggatt tattgggcgt aaagtgagcg taggtggtct ttcaagttgg    540
atgtgaaatt tcccggctta accggacgt gtcattcaat actgttggac tagagtacag    600
caggagaaaa cggaattccc ggtgtagtgg taaaatgcgt agatatcggg aggaacacca    660
gaggcgaagg cggttttcta ggttgtcact gacactgagg ctcgaaagcg tggggagcga    720
acagaattag atactctggt agtccacgcc ttaaactatg gacactaagt atagggagta    780
tcgaccctct ctgtgccgaa gctaacgctt aagtgtccc gcctggggag tacggtcgca    840
aggctaaaac tcaaaggaat tgacgggggc ccgcacaagc agcggagcgt gtggtttaat    900
tcgatgctac acgaagaacc ttaccaagat ttgacatgca tgaagtagtg aaccgaaagg    960
gaaacgacct gttaagtcag gagtttgcac aggtgctgca tggctgtcgt cagctcgtgc   1020
cgtgaggtgt ttggttaagt cctgcaacga gcgcaacccct gttgctagt taaatttttct   1080
agcgagactg ccccgcgaaa cggggaggaa gtgggggatg acgtcaagtc agcatggcct   1140
ttatatcttg gctacacac acgctacaat ggacagaaca ataggttgca acagtgtgaa   1200
ctggagctaa tcctcaaagc tgtcctcagt tcggattgca ggctgaaacc cgcctgcatg   1260
aagttggagt tgctagtaac cgcatatcag caaggtgcgg tgaatacgtt ctcgggcctt   1320
gtacacaccg cccgtcacgt catgaaagcc ggtaacactt gaagtcgatg tgccaacc     1378
```

<210> SEQ ID NO 4

<211> LENGTH: 1377
<212> TYPE: DNA
<213> ORGANISM: Dehalococcoides ethenogenes strain DAB

<400> SEQUENCE: 4

| | | | | | |
|---|---|---|---|---|---|
| gatgaacgct | agcggcgtgc | cttatgcatg | caagtcgaac | ggtcttaagc | aattaagata | 60 |
| gtggcgaacg | ggtgagtaac | gcgtaagtaa | cctacctcta | agtgggggat | agcttcggga | 120 |
| aactgaaggt | aataccgcat | gtggtgggcc | gacatatgtt | ggttcactaa | agccgtaagg | 180 |
| cgcttggtga | ggggcttgcg | tccgattagc | tagttggtgg | ggtaatggcc | taccaaggct | 240 |
| tcgatcggta | gctggtctga | gaggatgatc | agccacactg | ggactgagac | acggcccaga | 300 |
| ctcctacggg | aggcagcagc | aaggaatctt | gggcaatggg | cgaaagcctg | acccagcaac | 360 |
| gccgcgtgag | ggatgaaggc | tttcggggttg | taaacctctt | ttcataggga | agaataatga | 420 |
| cggtacctgt | ggaataagct | tcggctaact | acgtgccagc | agccgcggta | atacgtagga | 480 |
| agcaagcgtt | atccggattt | attgggcgta | aagtgagcgt | aggtggtctt | tcaagttgga | 540 |
| tgtgaaattt | cccggcttaa | ccgggacgag | tcattcaata | ctgttggact | agagtacagc | 600 |
| aggagaaaac | ggaattcccg | gtgtagtggt | aaaatgcgta | gatatcggga | ggaacaccag | 660 |
| aggcgaaggc | ggttttctag | gttgtcactg | acactgaggc | tcgaaagcgt | ggggagcgaa | 720 |
| cagaattaga | tactctggta | gtccacgcct | taaactatgg | acactaggta | tagggagtat | 780 |
| cgaccctctc | tgtgccgaag | ctaacgcttt | aagtgtcccg | cctggggagt | acggtcgcaa | 840 |
| ggctaaaact | caaaggaatt | gacgggggcc | cgcacaagca | gcggagcgtg | tggtttaatt | 900 |
| cgatgctaca | cgaagaacct | taccaagatt | tgacatgcat | gtagtagtga | actgaaaggg | 960 |
| gaacgacctg | ttaagtcagg | aacttgcaca | ggtgctgcat | ggctgtcgtc | agctcgtgcc | 1020 |
| gtgaggtgtt | tggttaagtc | ctgcaacgag | cgcaacccct | gttgctagtt | aaattttcta | 1080 |
| gcgagactgc | cccgcgaaac | ggggaggaag | gtggggatga | cgtcaagtca | gcatggcctt | 1140 |
| tatatcttgg | gctacacaca | cgctacaatg | gacagaacaa | taggttgcaa | cagtgtgaac | 1200 |
| tggagctaat | ccccaaagct | gtcctcagtt | cggattgcag | gctgaaaccc | gcctgcatga | 1260 |
| agttggagtt | gctagtaacc | gcatatcagc | atggtgcggt | gaatacgttc | tcgggccttg | 1320 |
| tacacaccgc | ccgtcacgtc | atgaaagccg | gtaacacttg | aagtcgatgt | gccaacc | 1377 |

<210> SEQ ID NO 5
<211> LENGTH: 1377
<212> TYPE: DNA
<213> ORGANISM: Dehalococcoides ethenogenes strain PIN

<400> SEQUENCE: 5

| | | | | | |
|---|---|---|---|---|---|
| gatgaacgct | agcggcgtgc | cttatgcatg | caagtcgaac | ggtcttaagc | aattaagata | 60 |
| gtggcgaacg | ggtgagtaac | gcgtaagtaa | cctacctcta | agtgggggat | agcttcggga | 120 |
| aactgaaggt | aataccgcat | gtggtgggcc | gacatatgtt | ggttcactaa | agccgtaagg | 180 |
| cgcttggtga | ggggcttgcg | tccgattagc | tagttggtgg | ggtaatggcc | taccaaggct | 240 |
| tcgatcggta | gctggtctga | gaggatgatc | agccacactg | ggactgagac | acggcccaga | 300 |
| ctcctacggg | aggcagcagc | aaggaatctt | gggcaatggg | cgaaagcctg | acccagcaac | 360 |
| gccgcgtgag | ggatgaaggc | tttcggggttg | taaacctctt | ttcataggga | agaataatga | 420 |
| cggtacctgt | ggaataagct | tcggctaact | acgtgccagc | agccgcggta | atacgtagga | 480 |
| agcaagcgtt | atccggattt | attgggcgta | aagtgagcgt | aggtggtctt | tcaagttgga | 540 |
| tgtgaaattt | cccggcttaa | ccgggacgag | tcattcaata | ctgttggact | agagtacagc | 600 |

```
aggagaaaac ggaattcccg gtgtagtggt aaaatgcgta gatatcggga ggaacaccag      660
aggcgaaggc ggttttctag gttgtcactg acactgaggc tcgaaagcgt ggggagcgaa      720
cagaattaga tactctggta gtccacgcct taaactatgg acactaggta tagggagtat      780
cgaccctctc tgtgccgaag ctaacgcttt aagtgtcccg cctggggagt acggtcgcaa      840
ggctaaaact caaaggaatt gacggggggcc cgcacaagca gcggagcgtg tggtttaatt      900
cgatgctaca cgaagaacct taccaagatt tgacatgcat gtagtagtga actgaaaggg      960
gaacgacctg ttaagtcagg aacttgcaca ggtgctgcat ggctgtcgtc agctcgtgcc     1020
gtgaggtgtt tggttaagtc ctgcaacgag cgcaacccct tgttgctagt taaatttcta     1080
gcgagactgc cccgcgaaac ggggaggaag gtggggatga cgtcaagtca gcatggcctt     1140
tatatcttgg gctacacaca cgctacaatg gacagaacaa taggttgcaa cagtgtgaac     1200
tggagctaat ccccaaagct gtcctcagtt cggattgcag gctgaaaccc gcctgcatga     1260
agttggagtt gctagtaacc gcatatcagc atggtgcggt gaatacgttc tcgggccttg     1320
tacacaccgc ccgtcacgtc atgaaagccg gtaacacttg aagtcgatgt gccaacc       1377
```

<210> SEQ ID NO 6
<211> LENGTH: 1377
<212> TYPE: DNA
<213> ORGANISM: Dehalococcoides ethenogenes strain DLL

<400> SEQUENCE: 6

```
gatgaacgct agcggcgtgc cttatgcatg caagtcgaac ggtcttaagc aattaagata       60
gtggcaaacg ggtgagtaac gcgtaagtaa cctacctcta agtgggggat agcttcggga      120
aactgaaggt aataccgcat gtggtgggcc gacataagtt ggttcactaa agccgtaagg      180
tgcttggtga ggggcttgcg tccgattagc tagttggtgg ggtaacggcc taccaaggct      240
tcgatcggta gctggtctga gaggatgatc agccacactg ggactgagac acggcccaga      300
ctcctacggg aggcagcagc aaggaatctt gggcaatggg cgaaagcctg acccagcaac      360
gccgcgtgag ggatgaaggc tctcgggttg taaacctctt ttcacaggga agaataatga      420
cggtacctgt ggaataagct tcggctaact acgtgccagc agccgcggta atacgtagga      480
agcaagcgtt atccggattt attgggcgta aagtgagcgt aggtggtctt tcaagttgga      540
tgtgaaattt cccggcttaa ccgggacgtg tcattcaata ctgttggact agagtacagc      600
aggagaaaac ggaattcccg gtgtagtggt aaaatgcgta gatatcggga ggaacaccag      660
aggcgaaggc ggttttctag gttgtcactg acactgaggc tcgaaagcgt ggggagcgaa      720
cagaattaga tactctggta gtccacgcct taaactatgg acactaggta tagggagtat      780
cgaccctctc tgtgccgaag ctaacgcttt aagtgtcccg cctggggagt acggtcgcaa      840
ggctaaaact caaaggaatt gacggggggcc cgcacaagca gcggagcgtg tggtttaatt      900
cgatgctaca cgaagaacct taccaagatt tgacatgcat gaagtagtga accgaaaggg      960
aaacgacctg ttaagtcagg agtttgcaca ggtgctgcat ggctgtcgtc agctcgtgcc     1020
gtgaggtgtt tggttaagtc ctgcaacgag cgcaacccct tgttgctagt taaatttcta     1080
gcgagactgc cccgcgaaac ggggaggaag gtggggatga cgtcaagtca gcatggcctt     1140
tatatcttgg gctacacaca cgctacaatg gacagaacaa taggttgcaa cagtgtgaac     1200
tggagctaat cctcaaagct gtcctcagtt cggattgcag gctgaaaccc gcctgcatga     1260
agttggagtt gctagtaacc gcatatcagc aaggtgcggt gaatacgttc tcgggccttg     1320
```

```
tacacaccgc  cgtcacgtc  atgaaagccg  gtaacacttg  aagtcgatgt  gccaacc       1377
```

<210> SEQ ID NO 7
<211> LENGTH: 1443
<212> TYPE: DNA
<213> ORGANISM: Dehalococcoides ethenogenes strain 195
<220> FEATURE:
<221> NAME/KEY: misc_feature
<222> LOCATION: (1353)..(1353)
<223> OTHER INFORMATION: N= unknown

<400> SEQUENCE: 7

```
gatgaacgct agcggcgtgc cttatgcatg caagtcgaac ggtcttaagc aattaagata     60
gtggcaaacg ggtgagtaac gcgtaagtaa cctacctcta agtgggggat agcttcggga   120
aactgaaggt aataccgcat gtgatgggct gacataagtc ggttcattaa agccgcaagg   180
tgcttggtga ggggcttgcg tccgattagc tagttggtgg ggtaatggtc taccaaggct   240
tcgatcggta gctggtctga gaggatgatc agccacactg gactgagac acgggccaga   300
ctcctacggg aggcagcagc aaggaatctt gggcaatggg cgaaagcctg acccagcaac   360
gccgcgtgag ggatgaaggc tttcggggttg taaacctctt ttcacaggga agaataatga   420
cggtacctgt ggaataagct tcggctaact acgtgccagc agccgcggta atacgtaggg   480
aagcaagcgt tatccggatt tattgggcgt aaagtgagcg taggtggtct ttcaagttgg   540
atgtgaaatt tcccggctta accgggacgt gtcattcaat actgttggac tagagtacag   600
caggagaaaa cggaattccc ggtgtagtgg taaaatgcgt agatatcggg aggaacacca   660
gaggcgaagg cggttttcta ggttgtcact gacactgagg ctcgaaagcg tggggagcga   720
acagaattag atactctggt agtccacgcc ttaaactatg gacactaggt atagggagta   780
tcgaccctct ctgtgccgaa gctaacgctt taagtgtccc gcctggggag tacggtcgca   840
aggctaaaac tcaaaggaat tgacggggggc ccgcacaagc agcggagcgt gtggtttaat   900
tcgatgctac acgaagaact taccaagatt tgacatgcat gaagtagtga accgaaaggg   960
aaacgacctg ttaagtcagg agtttgcaca ggtgctgcat ggctgtcgtc agctcgtgcc  1020
gtgaggtgtt gggttaagtc ctgcaacgag cgcaaccttg ttgctagtta aattttctag  1080
cgagactagc gagactgccc cgcgaaacgg ggaggaaggt ggggatgacg tcaagtcagc  1140
atggccttta tatcttgggc tacacacacg ctacaatgga cagaacaata ggttgcaaca  1200
gtgtgaactg gagctaatcc ccaaagctgt cctcagttcg gattgcaggc tgaaacccgc  1260
ctgcatgaag ttggagttgc tagtaaccgc atatcagcaa ggtgcggtga atacgttctc  1320
gggccttgta cacccgccc gtcacgtcat ganagccggt aacacttgaa gtcgatgtgc  1380
caaccgcaag gaggcagtcg ccgagggtgg gactggtaat tgggacgaag tcgtaacaag  1440
gta                                                                 1443
```

<210> SEQ ID NO 8
<211> LENGTH: 47
<212> TYPE: DNA
<213> ORGANISM: Dehalococcoides ethenogenes

<400> SEQUENCE: 8

```
tgtgrtgggc ygacatawgt yggttcayta aagccgyaag gygcttg                  47
```

<210> SEQ ID NO 9
<211> LENGTH: 20
<212> TYPE: DNA
<213> ORGANISM: Dehalococcoides ethenogenes

```
<400> SEQUENCE: 9
aagtcgaacg gtcttaagca                                              20

<210> SEQ ID NO 10
<211> LENGTH: 20
<212> TYPE: DNA
<213> ORGANISM: Dehalococcoides ethenogenes

<400> SEQUENCE: 10
cgtcattatt cttccctgtg                                              20

<210> SEQ ID NO 11
<211> LENGTH: 21
<212> TYPE: DNA
<213> ORGANISM: Dehalococcoides ethenogenes

<400> SEQUENCE: 11
gggaaacgac ctgttaagtc a                                            21

<210> SEQ ID NO 12
<211> LENGTH: 22
<212> TYPE: DNA
<213> ORGANISM: Dehalococcoides ethenogenes

<400> SEQUENCE: 12
ggattagctc cagttcacac tg                                           22

<210> SEQ ID NO 13
<211> LENGTH: 20
<212> TYPE: DNA
<213> ORGANISM: Dehalococcoides ethenogenes

<400> SEQUENCE: 13
aaatttaact agcaacaagg                                              20

<210> SEQ ID NO 14
<211> LENGTH: 19
<212> TYPE: DNA
<213> ORGANISM: Dehalococcoides ethenogenes

<400> SEQUENCE: 14
ggagtatcga ccctctctg                                               19

<210> SEQ ID NO 15
<211> LENGTH: 18
<212> TYPE: DNA
<213> ORGANISM: Dehalococcoides ethenogenes

<400> SEQUENCE: 15
gggagtatcg accctctc                                                18

<210> SEQ ID NO 16
<211> LENGTH: 18
<212> TYPE: DNA
<213> ORGANISM: Dehalococcoides ethenogenes

<400> SEQUENCE: 16
agtgaaccga aagggaaa                                                18

<210> SEQ ID NO 17
<211> LENGTH: 21
<212> TYPE: DNA
```

-continued

<213> ORGANISM: Dehalococcoides ethenogenes

<400> SEQUENCE: 17
gggttgtaaa cctcttttca c                                           21

<210> SEQ ID NO 18
<211> LENGTH: 20
<212> TYPE: DNA
<213> ORGANISM: Dehalococcoides ethenogenes

<400> SEQUENCE: 18
gttagcttcg gcacagagag                                             20

<210> SEQ ID NO 19
<211> LENGTH: 20
<212> TYPE: DNA
<213> ORGANISM: Dehalococcoides ethenogenes

<400> SEQUENCE: 19
tcagtgacaa cctagaaaac                                             20

<210> SEQ ID NO 20
<211> LENGTH: 17
<212> TYPE: DNA
<213> ORGANISM: Dehalococcoides ethenogenes

<400> SEQUENCE: 20
gatgaacgct agcggcg                                                17

<210> SEQ ID NO 21
<211> LENGTH: 18
<212> TYPE: DNA
<213> ORGANISM: Dehalococcoides ethenogenes

<400> SEQUENCE: 21
gtgccttatg catgcaag                                               18

<210> SEQ ID NO 22
<211> LENGTH: 21
<212> TYPE: DNA
<213> ORGANISM: Dehalococcoides ethenogenes

<400> SEQUENCE: 22
aataggttgc aacagtgtga a                                           21

<210> SEQ ID NO 23
<211> LENGTH: 22
<212> TYPE: DNA
<213> ORGANISM: Dehalococcoides ethenogenes

<400> SEQUENCE: 23
aatggacaga acaataggtt gc                                          22

<210> SEQ ID NO 24
<211> LENGTH: 21
<212> TYPE: DNA
<213> ORGANISM: Dehalococcoides ethenogenes

<400> SEQUENCE: 24
ggcacatcga cttcaagtgt t                                           21

<210> SEQ ID NO 25
<211> LENGTH: 20

```
<212> TYPE: DNA
<213> ORGANISM: Dehalococcoides ethenogenes

<400> SEQUENCE: 25
gggttgtaaa cctcttttca                                              20

<210> SEQ ID NO 26
<211> LENGTH: 20
<212> TYPE: DNA
<213> ORGANISM: Dehalococcoides ethenogenes

<400> SEQUENCE: 26
taaccgggac gwgtcattca                                              20

<210> SEQ ID NO 27
<211> LENGTH: 19
<212> TYPE: DNA
<213> ORGANISM: Dehalococcoides ethenogenes

<400> SEQUENCE: 27
gagtacagca ggagaaaac                                               19

<210> SEQ ID NO 28
<211> LENGTH: 21
<212> TYPE: DNA
<213> ORGANISM: Dehalococcoides ethenogenes

<400> SEQUENCE: 28
cctccttgcg gttggcacat c                                            21

<210> SEQ ID NO 29
<211> LENGTH: 19
<212> TYPE: DNA
<213> ORGANISM: Dehalococcoides ethenogenes

<400> SEQUENCE: 29
ggcagtctcg ctagaaaat                                               19

<210> SEQ ID NO 30
<211> LENGTH: 51
<212> TYPE: DNA
<213> ORGANISM: Dehalococcoides ethenogenes

<400> SEQUENCE: 30
tgwagtagtg aacmgaaagg graacgacct gttaagtcag garmttgcac a            51

<210> SEQ ID NO 31
<211> LENGTH: 18
<212> TYPE: DNA
<213> ORGANISM: Dehalococcoides ethenogenes

<400> SEQUENCE: 31
attttctacg cgagactg                                                18

<210> SEQ ID NO 32
<211> LENGTH: 27
<212> TYPE: DNA
<213> ORGANISM: Dehalococcoides ethenogenes

<400> SEQUENCE: 32
attttctacg cgagactagc gagactg                                      27

<210> SEQ ID NO 33
```

<211> LENGTH: 1542
<212> TYPE: DNA
<213> ORGANISM: Escherichia coli

<400> SEQUENCE: 33

```
aaattgaaga gtttgatcat ggctcagatt gaacgctggc ggcaggccta acacatgcaa      60
gtcgaacggt aacaggaaga agcttgcttc tttgctgacg agtggcggac gggtgagtaa     120
tgtctgggaa actgcctgat ggaggggggat aactactgga aacggtagct aataccgcat     180
aacgtcgcaa gaccaaagag gggaccttcg ggcctcttg ccatcggatg tgcccagatg      240
ggattagcta gtaggtgggg taacggctca cctaggcgac gatccctagc tggtctgaga     300
ggatgaccag ccacactgga actgagacac ggtccagact cctacgggag gcagcagtgg     360
ggaatattgc acaatgggcg caagcctgat gcagccatgc cgcgtgtatg aagaaggcct     420
tcgggttgta aagtactttc agcggggagg aagggagtaa agttaatacc tttgctcatt     480
gacgttaccc gcagaagaag caccggctaa ctccgtgcca gcagccgcgg taatacggag     540
ggtgcaagcg ttaatcggaa ttactgggcg taaagcgcac gcaggcggtt tgttaagtca     600
gatgtgaaat ccccgggctc aacctggaa ctgcatctga tactggcaag cttgagtctc       660
gtagaggggg gtagaattcc aggtgtagcg gtgaaatgcg tagagatctg gaggaatacc     720
ggtggcgaag cgcccccct ggacgaagac tgacgctcag gtgcgaaagc gtggggagca      780
aacaggatta gataccctgg tagtccacgc cgtaaacgat gtcgacttgg aggttgtgcc     840
cttgaggcgt ggcttccgga gctaacgcgt taagtcgacc gcctggggag tacggccgca     900
aggttaaaac tcaaatgaat tgacggggc ccgcacaagc ggtggagcat gtggtttaat       960
tcgatgcaac gcgaagaacc ttacctggtc ttgacatcca cggaagtttt cagagatgag    1020
aatgtgcctt cgggaaccgt gagacaggtg ctgcatggct gtcgtcagct cgtgttgtga    1080
aatgttgggt taagtcccgc aacgagcgca acccttatcc tttgttgcca gcggtccggc    1140
cgggaactca aaggagactg ccagtgataa actggaggaa ggtggggatg acgtcaagtc    1200
atcatggccc ttacgaccag ggctacacac gtgctacaat ggcgcataca agagaagcg     1260
acctcgcgag agcaagcgga cctcataaag tgcgtcgtag tccggattgg agtctgcaac    1320
tcgactccat gaagtcggaa tcgctagtaa tcgtggatca gaatgccacg gtgaatacgt    1380
tcccgggcct tgtacacacc gcccgtcaca ccatgggagt gggttgcaaa agaagtaggt    1440
agcttaacct tcgggagggc gcttaccact ttgtgattca tgactggggt gaagtcgtaa    1500
caaggtaacc gtagggaac ctgcggttgg atcacctcct ta                         1542
```

<210> SEQ ID NO 34
<211> LENGTH: 49
<212> TYPE: DNA
<213> ORGANISM: Dehalococcoides ethenogenes

<400> SEQUENCE: 34

```
aacccttgtt gctagttaaa ttttctagcg agactgcccc gcgaaacgg                  49
```

<210> SEQ ID NO 35
<211> LENGTH: 43
<212> TYPE: DNA
<213> ORGANISM: Dehalococcoides ethenogenes

<400> SEQUENCE: 35

```
tgtgatgggc tgacataagt cggttcatta aagccgcaag gtg                        43
```

-continued

<210> SEQ ID NO 36
<211> LENGTH: 43
<212> TYPE: DNA
<213> ORGANISM: Dehalococcoides ethenogenes

<400> SEQUENCE: 36
caccttgcgg ctttaatgaa ccgacttatg tcagcccatc aca        43

<210> SEQ ID NO 37
<211> LENGTH: 43
<212> TYPE: DNA
<213> ORGANISM: Dehalococcoides ethenogenes

<400> SEQUENCE: 37
tgtggtgggc cgacataagt tggttcacta aagccgtaag gtg        43

<210> SEQ ID NO 38
<211> LENGTH: 43
<212> TYPE: DNA
<213> ORGANISM: Dehalococcoides ethenogenes

<400> SEQUENCE: 38
caccttacgg ctttagtgaa ccaacttatg tcggcccacc aca        43

<210> SEQ ID NO 39
<211> LENGTH: 43
<212> TYPE: DNA
<213> ORGANISM: Dehalococcoides ethenogenes

<400> SEQUENCE: 39
tgtggtgggc cgacatatgt tggttcacta aagccgtaag gcg        43

<210> SEQ ID NO 40
<211> LENGTH: 43
<212> TYPE: DNA
<213> ORGANISM: Dehalococcoides ethenogenes

<400> SEQUENCE: 40
cgccttacgg ctttagtgaa ccaacatatg tcggcccacc aca        43

<210> SEQ ID NO 41
<211> LENGTH: 36
<212> TYPE: DNA
<213> ORGANISM: Dehalococcoides ethenogenes

<400> SEQUENCE: 41
agttaaattt tctagcgaga ctgccccgcg aaacgg        36

<210> SEQ ID NO 42
<211> LENGTH: 36
<212> TYPE: DNA
<213> ORGANISM: Dehalococcoides ethenogenes

<400> SEQUENCE: 42
ccgtttcgcg gggcagtctc gctagaaaat ttaact        36

<210> SEQ ID NO 43
<211> LENGTH: 29
<212> TYPE: DNA
<213> ORGANISM: Dehalococcoides ethenogenes

<400> SEQUENCE: 43
agttaaattt tctagcgaga ctgccccgc        29

```
<210> SEQ ID NO 44
<211> LENGTH: 29
<212> TYPE: DNA
<213> ORGANISM: Dehalococcoides ethenogenes

<400> SEQUENCE: 44
gcggggcagt ctcgctagaa aatttaact                              29

<210> SEQ ID NO 45
<211> LENGTH: 30
<212> TYPE: DNA
<213> ORGANISM: Dehalococcoides ethenogenes

<400> SEQUENCE: 45
ccttgttgct agttaaattt tctagcgaga                             30

<210> SEQ ID NO 46
<211> LENGTH: 30
<212> TYPE: DNA
<213> ORGANISM: Dehalococcoides ethenogenes

<400> SEQUENCE: 46
tctcgctaga aaatttaact agcaacaagg                             30

<210> SEQ ID NO 47
<211> LENGTH: 32
<212> TYPE: DNA
<213> ORGANISM: Dehalococcoides ethenogenes

<400> SEQUENCE: 47
gacatgcatg aagtagtgaa ccgaaaggga aa                          32

<210> SEQ ID NO 48
<211> LENGTH: 32
<212> TYPE: DNA
<213> ORGANISM: Dehalococcoides ethenogenes

<400> SEQUENCE: 48
tttccctttc ggttcactac ttcatgcatg tc                          32

<210> SEQ ID NO 49
<211> LENGTH: 30
<212> TYPE: DNA
<213> ORGANISM: Dehalococcoides ethenogenes

<400> SEQUENCE: 49
ggacgtgtca ttcaatactg ttggactaga                             30

<210> SEQ ID NO 50
<211> LENGTH: 30
<212> TYPE: DNA
<213> ORGANISM: Dehalococcoides ethenogenes

<400> SEQUENCE: 50
tctagtccaa cagtattgaa tgacacgtcc                             30

<210> SEQ ID NO 51
<211> LENGTH: 32
<212> TYPE: DNA
<213> ORGANISM: Dehalococcoides ethenogenes

<400> SEQUENCE: 51
tgttggacta gagtacagca ggagaaaacg ga                          32
```

```
<210> SEQ ID NO 52
<211> LENGTH: 32
<212> TYPE: DNA
<213> ORGANISM: Dehalococcoides ethenogenes

<400> SEQUENCE: 52
tccgttttct cctgctgtac tctagtccaa ca                         32

<210> SEQ ID NO 53
<211> LENGTH: 29
<212> TYPE: DNA
<213> ORGANISM: Dehalococcoides ethenogenes

<400> SEQUENCE: 53
ggcttaaccg ggacgtgtca ttcaatact                             29

<210> SEQ ID NO 54
<211> LENGTH: 29
<212> TYPE: DNA
<213> ORGANISM: Dehalococcoides ethenogenes

<400> SEQUENCE: 54
agtattgaat gacacgtccc ggttaagcc                             29

<210> SEQ ID NO 55
<211> LENGTH: 37
<212> TYPE: DNA
<213> ORGANISM: Dehalococcoides ethenogenes

<400> SEQUENCE: 55
aatttcccgg cttaaccggg acgtgtcatt caatact                    37

<210> SEQ ID NO 56
<211> LENGTH: 37
<212> TYPE: DNA
<213> ORGANISM: Dehalococcoides ethenogenes

<400> SEQUENCE: 56
agtattgaat gacacgtccc ggttaagccg ggaaatt                    37

<210> SEQ ID NO 57
<211> LENGTH: 31
<212> TYPE: DNA
<213> ORGANISM: Dehalococcoides ethenogenes

<400> SEQUENCE: 57
tgttaagtca ggagtttgca caggtgctgc a                          31

<210> SEQ ID NO 58
<211> LENGTH: 31
<212> TYPE: DNA
<213> ORGANISM: Dehalococcoides ethenogenes

<400> SEQUENCE: 58
tgcagcacct gtgcaaactc ctgacttaac a                          31

<210> SEQ ID NO 59
<211> LENGTH: 31
<212> TYPE: DNA
<213> ORGANISM: Dehalococcoides ethenogenes

<400> SEQUENCE: 59
```

```
cgcgtaagta acctacctct aagtggggga t                              31
```

<210> SEQ ID NO 60
<211> LENGTH: 31
<212> TYPE: DNA
<213> ORGANISM: Dehalococcoides ethenogenes

<400> SEQUENCE: 60

```
atcccccact tagaggtagg ttacttacgc g                              31
```